(12) United States Patent
Beijne et al.

(10) Patent No.: US 9,352,289 B2
(45) Date of Patent: May 31, 2016

(54) METHOD FOR PRODUCTION OF AN EMULSION

(75) Inventors: Petrus Bongers Martinus M Beijne, AT Vlaardingen (NL); Henelyta Santos Ribeiro, AT Vlaardingen (NL); Graeme Neil Irving, Wirral (GB); Michael John Egan, Liverpool (GB); Sabina Beijne, legal representative, AT Vlaardingen (NL)

(73) Assignee: Conopco, Inc., Englewood Cliffs, NJ (US)

( * ) Notice: Subject to any disclaimer, the term of this patent is extended or adjusted under 35 U.S.C. 154(b) by 522 days.

(21) Appl. No.: 13/996,631

(22) PCT Filed: Dec. 7, 2011

(86) PCT No.: PCT/EP2011/072112
§ 371 (c)(1),
(2), (4) Date: Oct. 31, 2013

(87) PCT Pub. No.: WO2012/089474
PCT Pub. Date: Jul. 5, 2012

(65) Prior Publication Data
US 2014/0113852 A1 Apr. 24, 2014

(30) Foreign Application Priority Data

Dec. 28, 2010 (EP) ..................................... 10197187

(51) Int. Cl.
| | | |
|---|---|---|
| C11D 3/00 | (2006.01) | |
| B01F 3/08 | (2006.01) | |
| B01F 7/00 | (2006.01) | |

(52) U.S. Cl.
CPC ............. *B01F 3/0811* (2013.01); *B01F 3/0807* (2013.01); *B01F 7/00816* (2013.01);
(Continued)

(58) Field of Classification Search
CPC .......... B01F 2003/0842; B01F 3/0811; B01F 7/00816; B01F 2215/0431; B01F 3/0807; B01F 2215/0014; B01F 2215/0031; B01F 2215/0032
See application file for complete search history.

(56) References Cited

U.S. PATENT DOCUMENTS

| 4,637,933 A | 1/1987 | Zabotto nee Arribau et al. |
| 5,192,577 A | 3/1993 | Masson |

(Continued)

FOREIGN PATENT DOCUMENTS

| DE | 19819273 | 11/1999 |
| DE | 19945203 | 12/2000 |

(Continued)

OTHER PUBLICATIONS

Bonsdorff-Nikander et al., Physical Stability of a Microcrystalline B-sitosterol suspension in Oil, European Journal of Pharmaceutical Sciences, 2003, pp. 173-179, 19.

(Continued)

*Primary Examiner* — Tony G Soohoo
(74) *Attorney, Agent, or Firm* — Greenberg Traurig, LLP

(57) ABSTRACT

The present invention has as an objective to provide a new emulsification method, which can produce concentrated water-continuous emulsion containing lipophilic compounds in a dispersed phase, with a very fine dispersed phase droplet size less than a micron, and a narrow size distribution of the dispersed phase. This objective has been met by a method wherein a water-continuous emulsion is made using a Controlled Deformation Dynamic Mixer or a Cavity Transfer Mixer.

13 Claims, 11 Drawing Sheets

(52) U.S. Cl.
CPC ....... *C11D3/0015* (2013.01); *B01F 2003/0842* (2013.01); *B01F 2215/0014* (2013.01); *B01F 2215/0031* (2013.01); *B01F 2215/0032* (2013.01); *B01F 2215/044* (2013.01); *B01F 2215/045* (2013.01); *B01F 2215/0431* (2013.01); *B01F 2215/0468* (2013.01); *B01F 2215/0481* (2013.01)

(56) References Cited

U.S. PATENT DOCUMENTS

| | | | |
|---|---|---|---|
| 5,885,590 | A | 3/1999 | Hunter et al. |
| 6,004,917 | A | 12/1999 | Akay et al. |
| 6,113,972 | A | 9/2000 | Corliss et al. |
| 6,132,076 | A | 10/2000 | Jana et al. |
| 6,416,751 | B1 | 7/2002 | Roulier et al. |
| 6,468,578 | B1 | 10/2002 | Bodor et al. |
| 6,551,619 | B1 | 4/2003 | Penkler et al. |
| 7,284,899 | B2 | 10/2007 | Nakano |
| 2003/0139543 | A1 | 7/2003 | Wilhelm |
| 2005/0124530 | A1 | 6/2005 | Creutz et al. |
| 2005/0259510 | A1* | 11/2005 | Thoma ................ B01F 3/04531 366/168.1 |
| 2006/0051479 | A1 | 3/2006 | Chiavazza et al. |
| 2008/0299200 | A1 | 12/2008 | Leser et al. |
| 2009/0181926 | A1 | 7/2009 | Akamatsu et al. |
| 2010/0220545 | A1 | 9/2010 | Brown |
| 2012/0113743 | A1 | 5/2012 | Brown et al. |
| 2013/0258801 | A1* | 10/2013 | Almeida Rivera .... B01F 3/0807 366/337 |

FOREIGN PATENT DOCUMENTS

| | | |
|---|---|---|
| EP | 194812 | 9/1986 |
| EP | 0297690 | 1/1989 |
| EP | 0605497 | 3/1996 |
| EP | 1749520 | 2/2007 |
| GB | 32106407 A | 4/1983 |
| GB | 2118854 | 11/1983 |
| JP | 5768124 | 4/1982 |
| JP | 58208400 | 12/1983 |
| JP | 198441 | 4/1989 |
| JP | 8503936 | 4/1996 |
| JP | 20031080 | 1/2003 |
| JP | 2008194692 | 8/2008 |
| WO | WO9305766 | 4/1993 |
| WO | WO9305768 | 4/1993 |
| WO | WO9528045 | 10/1995 |
| WO | WO9620270 A1 | 7/1996 |
| WO | WO0067728 A2 | 11/2000 |
| WO | WO2004084844 | 10/2004 |
| WO | WO2005035631 | 4/2005 |
| WO | WO2006063483 | 6/2006 |
| WO | WO2007105323 A1 | 9/2007 |
| WO | WO2008058593 | 5/2008 |
| WO | WO2008125380 | 10/2008 |
| WO | WO2010089320 | 8/2010 |
| WO | WO2010089322 A1 | 8/2010 |
| WO | WO2010091983 A1 | 8/2010 |
| WO | WO2010105922 | 9/2010 |

OTHER PUBLICATIONS

Christiansen et al., A Novel Method of Producing a Microcrystalline B-sitosterol Suspension in Oil, European Journal of Pharmaceutical Sciences, 2002, pp. 261-269, 15.
R. Engel, Formulation of phytosterols in emulsions for increased dose response in functional foods, Innovative Food Science & Emerging Technologies, 2005, pp. 233-237, 6.
Von Bonsdorff et al, Optimizing the Crystal Size and Habit of β-Sitosterol in Suspension, AAPS PharmSciTech, 2003, pp. 1-8, 4 (3).
PCT International Search Report and Written Opinion on Appliction No. PCT/EP2011/072112 dated Mar. 13, 2012.

* cited by examiner

METHOD FOR PRODUCTION OF AN EMULSION

The present invention relates to a method for producing emulsions using a Controlled Deformation Dynamic Mixer or Cavity Transfer Mixer.

BACKGROUND OF THE INVENTION

Mixing can be described as either distributive or dispersive. In a multi-phase material comprising discrete domains of each phase, distributive mixing seeks to change the relative spatial positions of the domains of each phase, whereas dispersive mixing seeks to overcome cohesive forces to alter the size and size distribution of the domains of each phase. Most mixers employ a combination of distributive or dispersive mixing although, depending on the intended application the balance will alter. For example a machine for mixing peanuts and raisins will be wholly distributive so as not to damage the things being mixed, whereas a blender/homogeniser will be dispersive.

Many different types of rotor/stator mixer are known. Stirring reactors such as those disclosed in US 2003/0139543 comprise a vessel with internally mounted mixing elements and are generally distributive in function. Other types of rotor-stator mixer (such as that disclosed in WO 2007/105323 are designed with the intention of forming fine emulsions and are dispersive in character.

EP 194 812 A2 discloses a cavity transfer mixer (CTM). Also WO 96/20270 describes a 'Cavity Transfer Mixer', comprising confronting surfaces, each having a series of cavities formed therein in which the surfaces move relatively to each other and in which a liquid material is passed between the surfaces and flows along a pathway successively passing through the cavities in each surface. The cavities are arranged on the relevant surfaces such that shear is applied to the liquid as it flows between the surfaces. In a typical embodiment the mixer comprises an outer sleeve and a close-fitting inner drum. The confronting surfaces of the sleeve and the drum are both provided with cavities disposed so that the cavities overlap forming sinuous and changing flow paths which change as the drum and the sleeve rotate relative to each other. This type of mixer has stator and rotor elements with opposed cavities which, as the mixer operates, move past each other across the direction of bulk flow through the mixer. In such mixers, primarily distributive mixing is obtained. Shear is applied by the relative movement of the surfaces in a generally perpendicular direction to the flow of material. In the typical embodiment described above, this is accomplished by relative rotation of the drum and the sleeve. In such a device there is relatively little variation in the cross-sectional area for flow as the material passes axially down the device. Generally, the cross-sectional area for flow varies by a factor of less than 3 through the apparatus.

WO 96/20270 also describes a novel mixer, hereinafter referred to as a 'Controlled Deformation Dynamic Mixer' (CDDM). In common with the CTM, type of mixer has stator and rotor elements with opposed cavities which, as the mixer operates, move past each other across the direction of bulk flow through the mixer. It is distinguished from the CTM in that material is also subjected to extensional deformation. The extensional flow and efficient dispersive mixing is secured by having confronting surfaces with cavities arranged such that the cross sectional area for bulk flow of the liquid through the mixer successively increases and decreases by a factor of at least 5 through the apparatus. In comparison with the embodiment of the CTM described above, the cavities of the CDDM are generally aligned or slightly offset in an axial direction such that material flowing axially along the confronting surfaces is forced through narrow gaps as well as flowing along and between the cavities. The CDDM combines the distributive mixing performance of the CTM with dispersive mixing performance. Thus, the CDDM is better suited to problems such as reducing the droplet size of an emulsion, where dispersive mixing is essential.

U.S. Pat. No. 6,468,578 B1 discloses the use of a cavity transfer mixer for creating an emulsion of water droplets in a continuous fat phase.

WO 2010/089320 A1, WO 2010/089322 A1, and WO 2010/091983 A1 disclose specific types of a distributive and dispersive mixing apparatus of the CDDM type or CTM type, comprising two confronting surfaces having cavities therein. These specific types may be used for the treatment of emulsions.

WO 2010/105922 A1 discloses that water-continuous emulsions of 5% silicone wax can be made in an aqueous solution that contains PET-POET polymer as emulsifier, by using a microfluidizer. This microfluidizer operates at high pressures of 1,200 bar to homogenise emulsions.

WO 96/28045 discloses a mixer with distributive and dispersive mixing zones, for making chewing gum.

US 2010/220545 A1 discloses a mixer with distributive and dispersive action, that can be used for emulsification.

WO 2008/125380 A1 discloses edible fat continuous spreads comprising phytosterols which are present in the form of elongated crystals, wherein the longest dimension is most preferably 2,000 micrometer.

WO 93/05768 and WO00/67728 disclose solid lipid particles having a diameter between 10 nanometer and 10 micrometer. These are produced by melting a lipid phase in an aqueous phase and subsequent homogenisation using a high pressure homogeniser.

SUMMARY OF THE INVENTION

These disclosures do not describe the production of concentrated oil-in-water emulsions, having a relatively high amount of dispersed phase. This would especially be of interest for the use of these emulsions as ingredient of consumer products like food products (e.g. margarines or other spreads), personal care products (e.g. skin creams), or home care products (e.g. liquid laundry detergents), cosmetic products (e.g. make-up like lipstick, eye and lip products), and pharmaceutical products (e.g. encapsulation of poor soluble lipophilic drugs for targeted delivery in vivo). It would especially be of interest to provide emulsions containing a finely dispersed oil phase that additionally contains phytosterols dispersed in the oil phase. Phytosterols have a very low solubility both in vegetable oils, as well as in water, especially at room temperature. These emulsions could be used as food ingredient to decrease LDL-cholesterol levels in humans. In order to be effective as LDL-cholesterol lowering agent, the dispersed phase containing phytosterols should be a finely dispersed as possible, and additionally the phytosterol is preferably not crystallised. If phytosterols crystallise the bio-accessability in vivo (in the gut) is less than when phytosterol is amorphous, due to large crystal size and shape of the crystals.

Similarly there is a desire to provide carotenoids, which are also very badly soluble both in vegetable oil at room temperature and in water. The carotenoids can act as anti-oxidants in vivo; additionally beta-carotene is a precursor for vitamin A.

Hence one of the objectives of the present invention is to provide a method for the production of oil-in-water emulsions, with a very fine dispersed lipid phase, and to provide emulsions which contain a relatively high concentration of lipophilic compounds that are poorly soluble in oil at room temperature and water. These emulsions can be used in food products, or home care products, or personal care products, or cosmetic products, or pharmaceutical products.

Moreover it is an objective of the present invention to provide a method to prepare the described emulsions with a low energy input and a high throughput.

We have now determined that one or more of these objectives can be met by a method wherein a lipophilic compound is brought into a liquid form, and emulsified using a CDDM or CTM type of mixer to a mean Sauter diameter of maximally 1 micrometer. This results in a finely dispersed phase of lipophilic materials, with high concentration of lipophilic compound, that can be used in foods, home care, personal care, cosmetic, or pharmaceutical products.

Moreover, by using a CDDM or CTM type of mixer, the required pressure is relatively low, while finely dispersed emulsions can be made which are stable. As compared to existing high pressure homogenisers the concentration of dispersed phase that can be achieved is higher, and the pressure required up to 20 times lower. This requires less heavy material specifications for design of an apparatus (to withstand high pressures), and less energy consumption to apply the pressure to the apparatus, and consequently a more environmentally friendly process and lower carbondioxide footprint.

Accordingly the present invention provides a method for production of a water-continuous emulsion, wherein the dispersed phase of the emulsion comprises a lipophilic compound, and wherein the mean Sauter diameter of the dispersed phase is less than 1 micrometer, and wherein the concentration of the dispersed phase is at least 20% by weight of the emulsion, and wherein the method comprises the steps:

a) mixing water and an oil-in-water emulsifier to form an aqueous phase; and
b) bringing the lipophilic compound into a liquid form to form a lipophilic phase; and
c) mixing the aqueous phase from step a) and the lipophilic phase from step b) in a distributive and dispersive mixing apparatus of the Controlled Deformation Dynamic Mixer type or Cavity Transfer Mixer type to create a water-continuous emulsion, and wherein the mixer is suitable for inducing extensional flow in a liquid composition,
and wherein the mixer comprises closely spaced relatively moveable confronting surfaces at least one having a series of cavities therein in which the cavities on each surface are arranged such that, in use, the cross-sectional area for flow of the liquid successively increases and decreases by a factor of at least 3 through the apparatus.

DETAILED DESCRIPTION

Figure 1:
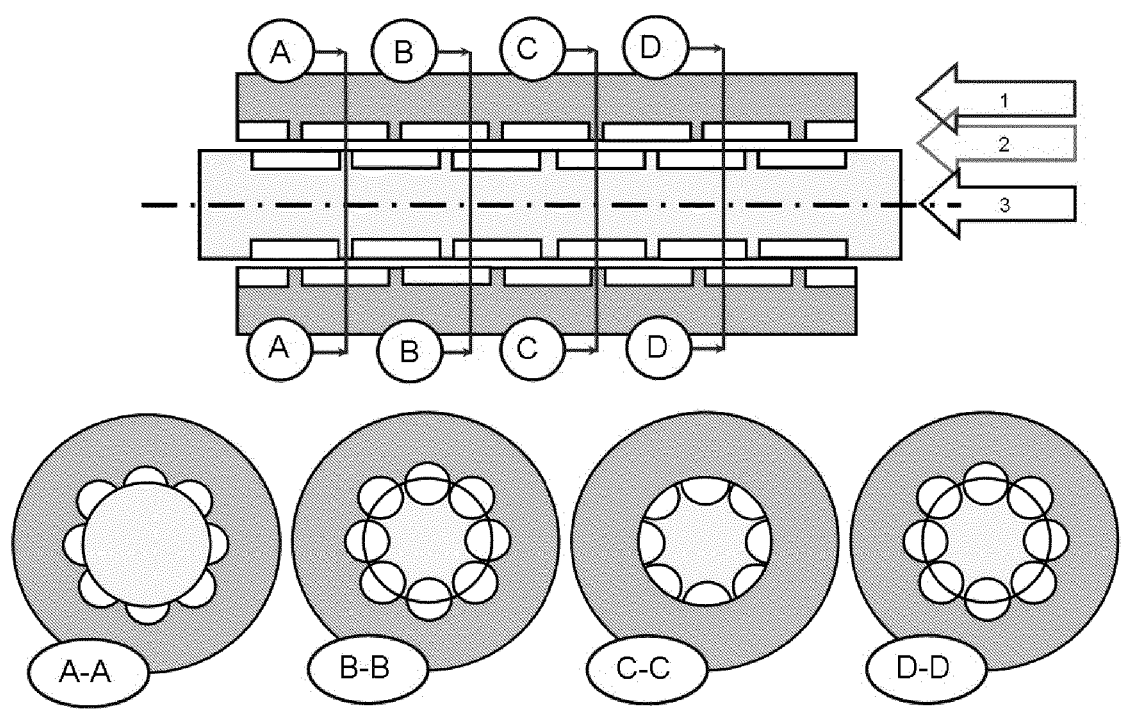
FIG. 1: Schematic representation of a Cavity Transfer Mixer (CTM); 1: stator, 2: annulus; 3: rotor; with cross-sectional views below.

Unless defined otherwise, all technical and scientific terms used herein have the same meaning as commonly understood by one of ordinary skill in the art.

All percentages, unless otherwise stated, refer to the percentage by weight. The abbreviation 'wt %' or '% (w/w)' refers to percentage by weight.

In the context of the present invention, the average particle diameter is generally expressed as the $d_{3,2}$ value, which is the Sauter mean diameter, unless stated otherwise. The Sauter mean diameter is the diameter of a sphere that has the same volume/surface area ratio as a particle of interest. Also the $d_{4,3}$ value, which is the volume weighted mean diameter, is used herein. The volume based particle size equals the diameter of the sphere that has same the same volume as a given particle.

The polydispersity, i.e. the width of the particle size distribution, is determined by the Span:

Span=[particle diameter at 90% cumulative size]–
[particle diameter at 10% cumulative size]/[particle diameter at 50% cumulative size].

The span is a dimensionless number which illustrates whether or not the spread of the distribution is narrow or wide. A small span indicates a narrow size distribution.

In case a range is given, the given range includes the mentioned endpoints.

An edible or a food product in the context of the present invention encompasses, but is not limited to, food products including spreads, salad dressings, dairy products, beverages, dietetic foods, dietary supplements, pharmaceutic compositions, and others. The products may contain ingredients common in the art and may be made by methods common in the art.

In the context of the present invention, a home care product is a product which is normally used for cleaning items such as hard surfaces in the home, or cleaning items such as the dishes and other kitchen hardware, or may be laundry detergents in liquid or solid form (powders, tablets), or may be laundry conditioners. Examples of such products are liquid or gel cleaners for the kitchen, bathroom, or toilet, and dishwashing liquid. The home care products may contain microcapsules containing perfumes and/or fragrances, or cleaning aids. In case of laundry detergents or laundry conditioners the microcapsules may contain a perfume or fragrance, and the microcapsules may be deposited on the garments during the laundering process. Subsequently the microcapsules may release the perfume and/or fragrance during the wearing of the garments, or may be released during for example ironing of the garments.

In the context of the present invention a personal care product is a product which is used by a consumer for cleaning, hygiene, and/or beauty. Cosmetic products in the context of the present invention encompasses, but is not limited to, skin creams, body lotions, shampoos, hair conditioners, toothpastes, deodorants, hair styling products, personal soap bars, and liquid personal soaps. In the case of these products the microcapsules may contain perfumes and/or fragrances, or may for example contain one ore more compounds which are beneficial for the health and/or beauty of the skin.

Cavity Transfer Mixers (CTMs)

Similar as in WO 96/20270, CTMs are defined as mixers comprising confronting surfaces, at least one of the surfaces, preferably both surfaces, having a series of cavities formed therein in which the surfaces move relatively to each other and in which a liquid material is passed between the surfaces and flows along a pathway successively through the cavities in each surface. The cavities are arranged on the relevant surfaces such that shear is applied to the liquid as it flows between the surfaces. The cavities are arranged on the respective surfaces such that there is a relatively small change in the effective cross sectional flow area as the material passes through the mixer. In such mixers, primarily distributive mixing is obtained. Generally the cross-sectional area for flow varies by a factor of less than 3 through the apparatus. Shear is applied by the relative movement of the surfaces in a generally perpendicular direction to the flow of material there between.

Here we exemplify CTMs by reference to FIG. 1 which displays an axial section and four transverse radial sections through a CTM configured as a 'concentric cylinder' device and comprising an inner rotor journalled within an outer stator. Briefly, the axial section shows the relative axial positions of rotor and stator cavities which are time invariant, whereas the transverse sections (A-A, B-B, C-C, D-D) demonstrate the axial variation in the available cross-sectional area for material flow axially:

A-A through the stator cavities in positions in which those stator cavities are confronted by 'rotor rings', ie the circumferentially extending rings which separate successive rings of rotor cavities;

B-B between the stator cavities and the rotor cavities in positions in which the former are confronted by the latter;

C-C through the rotor cavities in positions in which those rotor cavities are confronted by 'stator rings', ie the circumferentially extending rings which separate successive rings of stator cavities;

D-D between the rotor cavities and the stator cavities in positions in which the former are confronted by the latter.

The key feature to note is that there is little variation in the cross-sectional area for flow as the material passes axially down the device.

Controlled Deformation Dynamic Mixers (CDDMs)

Similar as in WO 96/20270, CDDMs are distinguished from CTMs by their description as mixers: comprising confronting surfaces, at least one of the surfaces, preferably both surfaces, having a series of cavities formed therein in which the surfaces move relatively to each other and in which a liquid material is passed between the surfaces and flows along a pathway successively through the cavities in each surface and is subjected to extensional deformation and/or shear deformation and preferably both extensional and shear deformation. The cavities are arranged on the relevant surfaces such that shear is applied by the relative movement of the surfaces in a generally perpendicular direction to the flow of material there between. In addition to shear, significant extensional flow and efficient distributive and dispersive mixing may be secured by providing an apparatus having confronting surfaces and cavities therein in which the cavities are arranged such that the cross sectional area for flow of the liquid successively increases and decreases by a factor of at least 5 through the apparatus.

Figure 2:
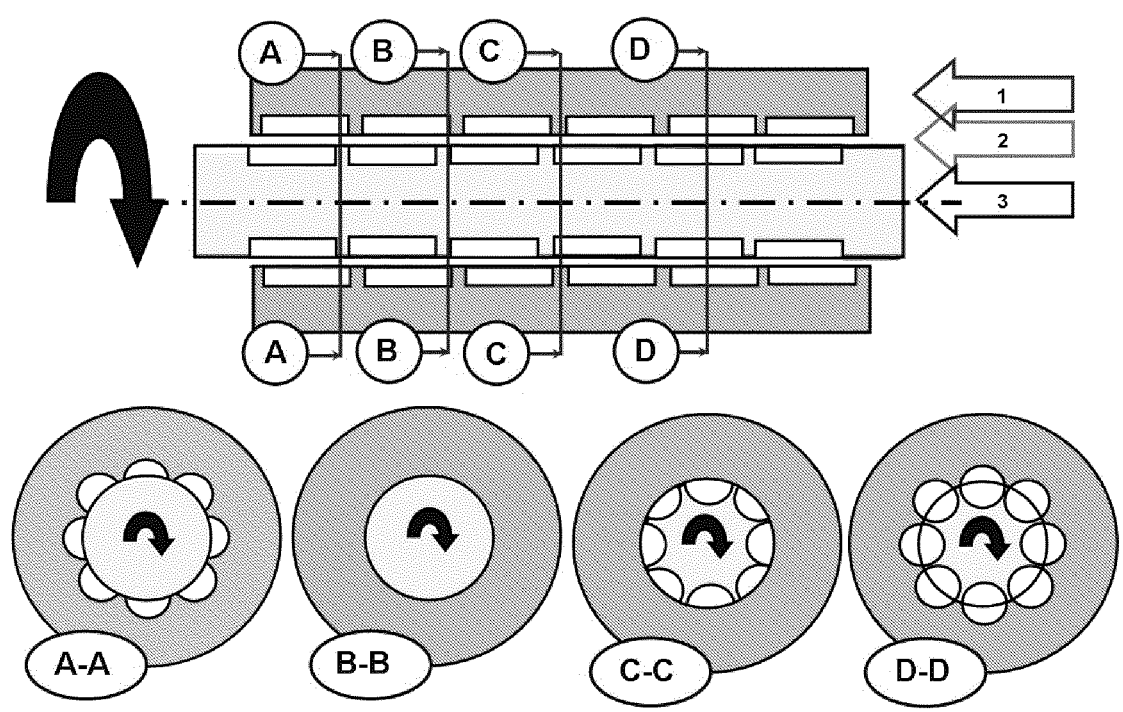
FIG. 2: Schematic representation of a Controlled Deformation Dynamic Mixer (CDDM); 1: stator, 2: annulus; 3: rotor; with cross-sectional views below.

Here we exemplify CDDMs by reference to FIG. 2 which displays an axial section and four transverse radial sections through a CDDM configured as a 'concentric cylinder' device comprising an inner rotor journalled within an outer stator. Briefly, the axial section shows the relative axial positions of rotor and stator cavities which are time invariant, whereas the transverse sections (A-A, B-B, C-C, D-D) demonstrate the axial variation in the available cross-sectional area for material flow axially:

A-A through the stator cavities in positions in which those stator cavities are confronted by 'rotor rings', ie the circumferentially extending rings which separate successive rings of rotor cavities;

B-B between the stator cavities and the rotor cavities through the annulus formed in those positions in which the 'rotor rings' are confronted by the 'stator rings';

C-C through the rotor cavities in positions in which those rotor cavities are confronted by 'stator rings', ie the circumferentially extending rings which separate successive rings of stator cavities;

D-D between the rotor cavities and the stator cavities in positions in which the former are confronted by the latter.

Clearly there is a significant variation in the cross-sectional area for flow as the material passes axially through the annulus formed between the 'rotor rings' and the 'stator rings' (BB), and between confronting rotor cavities and stator cavities (D-D).

terephthalate-co-polyoxyethylene terephthalate, as described in WO 2010/105922 A1). 'PET' is lipophilic, 'POET' is hydrophobic. The chemical structure of PET-POET is:

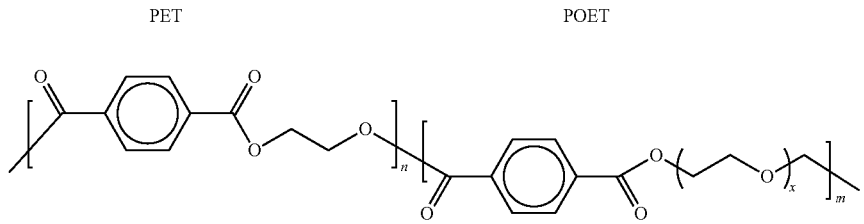

By comparison of FIG. 1 and FIG. 2, it will be understood that CDDMs are distinguished from CTMs by the relative position of the rotor and stator and consequent incorporation of an extensional component of flow. Hence CDDMs combine the distributive mixing performance of CTMs with the dispersive mixing performance of multiple expansion-contraction static mixers.

Method for Production of Emulsion

The present invention provides a method for production of a water-continuous emulsion, wherein the dispersed phase of the emulsion comprises a lipophilic compound, and wherein the mean Sauter diameter of the dispersed phase is less than 1 micrometer, and wherein the concentration of the dispersed phase is at least 20% by weight of the emulsion, and wherein the method comprises the steps:
a) mixing water and an oil-in-water emulsifier to form an aqueous phase; and
b) bringing the lipophilic compound into a liquid form to form a lipophilic phase; and
c) mixing the aqueous phase from step a) and the lipophilic phase from step b) in a distributive and dispersive mixing apparatus of the Controlled Deformation Dynamic Mixer type or Cavity Transfer Mixer type to create a water-continuous emulsion,
and wherein the mixer is suitable for inducing extensional flow in a liquid composition,
and wherein the mixer comprises closely spaced relatively moveable confronting surfaces at least one having a series of cavities therein in which the cavities on each surface are arranged such that, in use, the cross-sectional area for flow of the liquid successively increases and decreases by a factor of at least 3 through the apparatus.

In step a) preferably the temperature of the mixture is maximally 110° C. Increase of temperature may be useful to improve the dispersing of the emulsifier. Moreover at increased temperature, the subsequent emulsification may be performed more efficiently than at lower temperatures, when all compounds to be mixed are in liquid state. Preferably this step a) is performed at atmospheric pressure. Preferably the temperature is maximally 100° C., more preferred maximally 95° C.

The emulsifier may be any compound which can be used to emulsify oils in water. Preferably the HLB value of the emulsifier is larger than 7, preferably from 8 to 18. The HLB value (hydrophilic-lipophilic balance) of an emulsifier is a measure of the degree to which it is hydrophilic or lipophilic, and determines the emulsifying ability of the emulsifer of oil in water, or water in oil. Examples of such emulsifiers are polyoxyethylene (20) sorbitan monolaurate, commercially known as Tween®20, and the polymer PET-POET (polyethylene Other preferred emulsifiers include sugar esters with HLB values larger than 7, or any hydrophilic emulsifier which is not sensitive to temperature.

Preferably the lipophilic compound in step b) are lipophilic materials which often are from natural origin, but they may also be synthetic compounds.

In step b) the lipophilic compound is brought in liquid form, in order to be able to finely disperse the lipophilic phase in the subsequent step c). When in liquid form, the lipophilic phase which is formed in step b) will break up in droplets in the mixing step in step c) and will be dispersed in the aqueous phase from step a). Preferably in step b) the lipophilic compound is brought into a liquid form by increase of temperature to melt the compound. The temperature required will depend on the specific lipophilic compound, preferably the temperature in step b) is maximally 160° C., preferably maximally 150° C., preferably maximally 110° C., preferably maximally 95° C.

Preferably the lipophilic compound comprises lecithin, fatty acid, monoglyceride, diglyceride, triglyceride, phytosterol, phytostanol, phytosteryl-fatty acid ester, phytostanyl-fatty acid ester, wax, fatty alcohol, carotenoid, oil-soluble colourant, oil-soluble vitamin, oil-soluble flavour, oil-soluble fragrance, oil-soluble drugs, mineral oils or derivatives, petrolatum or derivatives, or silicon oils or derivatives, or combinations of these compounds. Also combinations of these compounds are within the scope of the present invention.

Oils and fats such as dairy fats, or vegetable oils or algae oils are a common source for monoglycerides, diglycerides, and triglycerides. Examples of fat-soluble vitamins are vitamin A, vitamin D2, vitamin D3, vitamin E, and vitamin K. These vitamins include all compounds which function as the respective vitamin. The carotenoids include alpha-carotene, beta-carotene, lycopene, canthaxanthin, astaxanthin, lutein, and zeaxanthin, as well as their esterified forms. These compounds could be used as ingredients of food products.

Also materials like mineral oils, petrolatum, and silicon oils, and derivatives of these compounds are preferred compounds which could be used in this invention as the lipophilic compound. These compounds could be used as ingredients in personal care products such as skin creams and body lotions, or home care products such as laundry detergent compositions, especially liquid laundry detergent compositions.

Lecithin: is a general term for a mixture which may originate from plant origin (e.g. soy bean) or animal origin (e.g. egg yolk), and is used as emulsifier. The most important compounds in lecithin are phosphatidylcholine, phosphatidylethanolamine, and phosphatidylinositol. In commercially available lecithins also free fatty acids, triglycerides and mono- and diglycerides can be present. The nature of the phosphoric group and said fatty acids determine the emulsification properties of lecithin.

Fatty acid: fatty acids suitable in the present invention are C3 fatty acids and longer chains, preferably at least C12, up to preferably C26. The aliphatic tail may be saturated or unsaturated. The chain can be unbranched or have branches like a hydroxy, methyl- or ethyl group. The fatty acid suitable in the present invention consists of minimum 3 carbon atoms and a maximum of 26.

Monoglyceride: an ester of glycerol and one fatty acid, wherein the fatty acid may be as described above.

Diglyceride: an ester of glycerol and two fatty acids, wherein the fatty acids may be as described above.

Triglyceride: a glycerol which is esterified with three fatty acids, as described above. The fatty acids may be saturated, or monounsaturated or polyunsaturated. In the context of the present invention, triglycerides are understood to be edible oils and fats. As used herein the term 'oil' is used as a generic term for oils and fats either pure or containing compounds in solution. Oils can also contain particles in suspension.

As used herein the term 'fats' is used as a generic term for compounds containing more than 80% triglycerides. They can also contain diglycerides, monoglycerides and free fatty acids. In common language, liquid fats are often referred to as oils but herein the term fats is also used as a generic term for such liquid fats. Fats include: plant oils (for example: allanblackia oil, apricot kernel oil, arachis oil, arnica oil, argan oil, avocado oil, babassu oil, baobab oil, black seed oil, blackberry seed oil, blackcurrant seed oil, blueberry seed oil, borage oil, calendula oil, camelina oil, camellia seed oil, castor oil, cherry kernel oil, cocoa butter, coconut oil, corn oil, cottonseed oil, evening primrose oil, grapefruit oil, grape seed oil, hazelnut oil, hempseed oil, illipe butter, lemon seed oil, lime seed oil, linseed oil, kukui nut oil, macadamia oil, maize oil, mango butter, meadowfoam oil, melon seed oil, moring a oil, mowrah butter, mustard seed oil, olive oil, orange seed oil, palm oil, palm kernel oil, papaya seed oil, passion seed oil, peach kernel oil, plum oil, pomegranate seed oil, poppy seed oil, pumpkins seed oil, rapeseed (or canola) oil, red raspberry seed oil, rice bran oil, rosehip oil, safflower oil, seabuckthorn oil, sesame oil, shea butter, soy bean oil, strawberry seed oil, sunflower oil, sweet almond oil, walnut oil, wheat germ oil); fish oils (for example: sardine oil, mackerel oil, herring oil, cod-liver oil, oyster oil); animal oils (for example: butter or conjugated linoleic acid, lard or tallow); or any mixture or fraction thereof. The oils and fats may also have been modified by hardening, fractionation, chemical or enzymatical interesterification or by a combination of these steps.

Phytosterol: a group of steroid alcohols, phytochemicals naturally occurring in plants. At room temperature they are white powders with mild, characteristic odor, insoluble in water and soluble in alcohols. They can be used to decrease the LDL-cholesterol level in plasma in humans.

Phytostanol: similar to the phytosterol, a group of steroid alcohols, phytochemicals naturally occurring in plants. They may also be obtained by hardening a phytosterol.

Phytosteryl-fatty acid ester: a phytosterol which has been modified by esterifying it with a fatty acid.

Phytostanyl-fatty acid ester: a phytostanol which has been modified by esterifying it with a fatty acid.

Waxes: a wax is a non-glyceride lipid substance having the following characteristic properties: plastic (malleable) at normal ambient temperatures; a melting point above approximately 45° C.; a relatively low viscosity when melted (unlike many plastics); insoluble in water but soluble in some organic solvents; hydrophobic. Waxes may be natural or artificial, but natural waxes, are preferred. Beeswax, candellila and carnauba (vegetable waxes), chinese wax, epicuticular waxes, japan wax, jojoba oil, lanolin or woll wax, montan wax, ouricury wax, paraffin (a mineral wax), petroleum jelly, retamo wax, rice bran wax, shellac wax, spermaceti, sugarcane wax are commonly encountered waxes which occur naturally. Some artificial materials that exhibit similar properties are also described as wax or waxy. Chemically speaking, a wax may be an ester of ethylene glycol (ethane-1,2-diol) and two fatty acids, as opposed to fats which are esters of glycerol (propane-1,2,3-triol) and three fatty acids. It may also be a combination of fatty alcohols with fatty acids, alkanes, ethers or esters. Preferred waxes are one or more waxes chosen from candellila, carnauba wax, shellac wax or beeswax or silicon wax or their synthetic equivalents. Also paraffin-based synthetic waxes are within the scope of the present invention. It may also include polyethylene waxes, polymerized alpha-olefins, chemically modified waxes—usually esterified, or saponified substituted amide waxes.

Most preferred, the lipophilic compound is selected from the group of phytosterols, carotenoids, and derivatives of these compounds. Also mixtures of these compounds are within the scope of the invention. These compounds are especially of interest to be ingredients of food products, as they have a nutritional benefit when consumed. The phytosterols are compounds known for its LDL-cholesterol lowering effect upon consumption.

The term phytosterol and plant sterols are considered to by synonymous, and they can also be referred to as 'sterols'. The phytosterols can be classified in three groups, which are the 4-desmethylsterols, 4-monomethylsterols and 4,4'-dimethylsterols. In oils they mainly exist as free sterols and sterol esters of fatty acids although sterol glucosides and acylated sterol glucosides are also present. There are three major phytosterols namely beta-sitosterol, stigmasterol and campesterol.

The respective 5 alpha-saturated derivatives (the 'stanols') such as sitostanol, campestanol and ergostanol and their derivatives are also encompassed in the term phytosterol.

Preferably the phytosterol is selected from the group comprising beta-sitosterol, beta-sitostanol, campesterol, campestanol, stigmasterol, brassicasterol, brassicastanol or a mixture thereof. Suitable sources of phytosterols are for example derived from soy bean or tall oil.

Phytosterols are difficult to formulate into food products in their free form due to their poor solubility in fats and immiscibility in water which may result in food products having poor organoleptic properties, e.g. a sandy mouth feel. This has been partially mitigated in the prior art by esterification of the phytosterol with fatty acids, but calls for additional processing steps and hence an increase in costs. It has also been described in the literature that by using very small phytosterol particles it may be possible to alleviate to a certain extent the negative impact of phytosterol on the organoleptic properties. Typically the size of such particles is in the order of tens of micron, however particle sizes above one micron are poorly bio-accessible in the gastro-intestinal tract. Furthermore it has been described in the literature that the negative influence of phytosterol on the organoleptic properties in emulsions may be mitigated to a certain extent by emulsifying the phytosterol with emulsifier.

In the context of this invention the term phytosterol refers to the free phytosterol, i.e. the non-esterified phytosterol, unless specified otherwise.

In step b) preferably the lipophilic compound is mixed with a non-aqueous phase. By this mixing, the lipophilic compound is brought into liquid form by dissolving in the non-aqueous phase. Preferably this step is carried out while the temperature of the mixture is increased, to a temperature of maximally 160° C., preferably maximally 150° C., preferably maximally 110° C., preferably maximally 95° C.

A 'non-aqueous phase' as used in this context may relate to a liquid at ambient conditions (temperature about 20° C., atmospheric pressure), and where said liquid has a tendency to flow, as determined by having a loss modulus G" larger than the storage modulus G' at shear rates y (gamma) ranging from 1 per second to 500 per second. The non-aqueous phase may also be solid at room temperature, and made liquid by melting. The non-aqueous character is defined as the material not being able to dissolve more than 10% by weight in water under ambient conditions, preferably less than 5% by weight, preferably less than 1% by weight, preferably less than 0.5% by weight, preferably less than 0.2% by weight.

Preferably the non-aqueous phase comprises a vegetable oil, for example sunflower oil, palm oil, olive oil, rapeseed oil, or any other suitable oil or combinations of oils, or a wax (e.g. candellila wax, carnauba wax, or other waxes as herein described before). The oil may be liquid at room temperature, or alternatively may be solid at room temperature, in which case the oil should be melted first by increasing the temperature. A fat or oil from animal origin, such as fish oil, dairy fat, lard, or tallow, may be used as well. Such a vegetable oil or animal oil or algae oil obtained from step b) may be used as an ingredient of food products.

The optional non-aqueous phase may also be chosen from materials like mineral oils, petrolatum, and silicon oils, and derivatives of these compounds, and combinations of these. In that case the structured non-aqueous phase obtained from step b) may be used as an ingredient of home care or personal care products.

Preferably the concentration of the lipophilic compound in the non-aqueous phase is at least 5% by weight, preferably at least 10% by weight, preferably at least 20% by weight. Although the lipophilic compound may be poorly soluble in the non-aqueous phase, such as in case of carotenoids and phytosterols (e.g. in vegetable oils at room temperature), such a high concentration of lipophilic compound in a non-aqueous phase can be used in the method of the invention. A high concentration has the advantage that the final emulsion will contain a high amount of the lipophilic compound in a non-aqueous phase, and this non-aqueous phase is dispersed as a colloidal dispersion, as the droplet size is very small after step c). The lipophilic compound may be in crystalline form when mixed with the non-aqueous phase.

Upon dissolving the lipophilic compound in the liquid, the lipophilic compound will be in amorphous form. The concentration of the lipophilic compound may be so high, that after emulsification and upon cooling of the emulsion, the dispersed phase becomes supersaturated. Due to the small droplet size of the dispersed phase, the hydrophobic compound may remain in an amorphous state, and does not, or only limitedly, crystallise. It may even happen that the lipophilic compound remains in a liquid state or metastable state. Less crystallisation means that the droplets remain stable; as otherwise crystals may grow and may form needles which stick through and interfere with the interface between the oil droplet and the continuous aqueous phase, breaking up the droplets. Therefore the method according to the invention not only leads to improved stability of the emulsion, but also to dispersed lipophilic compounds which are not crystalline.

In case of phytosterols, amorphous phytosterol is easier incorporated in micelles in the intestinal tract than crystallised phytosterol. As part of the micelles, the function of phytosterols is to influence the adsorption and desorption of LDL-cholesterol from an to the plasma, leading to decreased LDL-cholesterol levels in the plasma. Hence one of the advantages of the method of the invention is that when sterols are mixed with a non-aqueous phase and subsequently emulsified, the amorphous phase may lead to improved bio-accessability and/or bio-availability as compared to crystallised sterols.

Step c) will preferably be carried out at the temperature that is obtained after mixing the aqueous phase from step a) and the lipophilic phase from step b). Prior to step c) a pre-emulsion may be made to mix the aqueous phase from and the lipophilic phase, in order to improve the emulsification in step c). This premixing may be carried out under temperature control, to keep the mixture liquid. The temperature in this optional premixing step is preferably maximally 110° C., preferably maximally 100° C. (when at atmospheric pressure), preferably maximally 95° C. The temperature of the emulsification in step c) may be controlled, in order to guarantee that the aqueous phase from step a) and the lipophilic phase from step b) remain liquid. Usually the mixing in step c) will be carried out at the temperature of the premixes from step a) and b). Usually during the emulsification step the temperature of the mix will not decrease, due to the energy input into the mixing process. Hence the temperature of the emulsion coming out of step c) may be increased.

The emulsion obtained from step c) may be used as an ingredient of food products, or personal care products, or home care products, or cosmetic products, or pharmaceutical products. In that case the emulsion from step c) may be brought into contact with any of the other ingredients of such a product. Subsequently the normal preparation process for such a product can be carried out. Prior to using the emulsion from step c), the mixture from step c) may be cooled. This optional cooling may be done using any suitable method.

Due to the incorporation of lipophilic compounds in the non-aqeuous liquid, the dispersed phase droplets may become solid after step c), especially when the emulsion obtained from step c) is cooled. The method according to the invention then can be regarded to be an encapsulation process, wherein the lipophilic compound is encapsulated in the non-aqueous phase. Hence the method according to the invention preferably also provides a method for encapsulation of lipophilic compounds.

The mean Sauter diameter of the dispersed phase obtained after step c) is less than 1 micrometer. Preferably the mean Sauter diameter of the dispersed phase is less than 500 nanometer. Even more preferred the mean Sauter diameter of the dispersed phase is less than 400 nanometer, more preferred less than 300 nanometer. Preferably the mean Sauter diameter of the dispersed phase is at least 100 nanometer, more preferred at least 150 nanometer. When the average size of the dispersed phase is as small as these values, the emulsion may become transparent, as the size of the dispersed droplets is smaller than the wavelength of visible light. This property may be used to formulate interesting products for the consumer, with properties which were not attainable earlier.

The concentration of dispersed phase in the emulsion that is obtained from step c) is at least 20% by weight of the emulsion. One of the advantages of the method according to the invention is that the concentration of dispersed phase that can be obtained is high. Especially when compared to emulsions produced by high pressure homogenisers. Preferably the concentration of the dispersed phase is at least 40% by weight of the emulsion, preferably at least 50% of the emulsion. Preferably the dispersed phase comprises at least 60% by weight of the emulsion. Preferably the emulsion contains maximally 95% by weight of the emulsion of dispersed phase, preferably maximally 85% by weight, preferably maximally 75% by weight. Such highly dispersed emulsions have the advantage that when used in food products, or personal care products, or home care products, or cosmetic products, or pharmaceutical products, only a relatively small amount of the emulsion is required to formulate the products.

Another advantage of the production of the concentrated water-continuous emulsions (both high dispersed phase concentration, as well as high concentration of lipophilic compound in non-aqueous phase), as compared to more dilute emulsions as processed in for example high pressure homogenisers, is the reduction of energy required to heat the aqueous phase and the lipophilic phase. This is due to the large difference in heat capacity between water and lipophilic compounds and non-aqueous phases.

CDDM Apparatus and/or CTM Apparatus

In step c) the water-continuous emulsion is prepared by mixing the aqueous phase from step a) and the lipophilic phase from step b) in a distributive and dispersive mixing apparatus of the Controlled Deformation Dynamic Mixer type or Cavity Transfer Mixer type, and wherein the mixer is suitable for inducing extensional flow in a liquid composition, and wherein the mixer comprises closely spaced relatively moveable confronting surfaces at least one having a series of cavities therein in which the cavities on each surface are arranged such that, in use, the cross-sectional area for flow of the liquid successively increases and decreases by a factor of at least 3 through the apparatus.

For the purposes of understanding the operation of the CTM or CDDM in general, the disclosure of WO 96/20270 is incorporated herein by reference. Regions of distributive mixing (where the flow path is wide) comprises CTM-like cavities moving across each other in a direction perpendicular to the bulk flow of liquid. Between these regions of distributive mixing are regions in which the flow path is narrower and the flow is more extensional. It is possible for a mixer used in the method according to the invention to be provided with one on more regions in which the juxtaposition is such that the arrangement is CTM-like and one or more regions in which the arrangement is CDDM-like. Preferably a CDDM apparatus is used in the method according to the invention.

Figure 10:
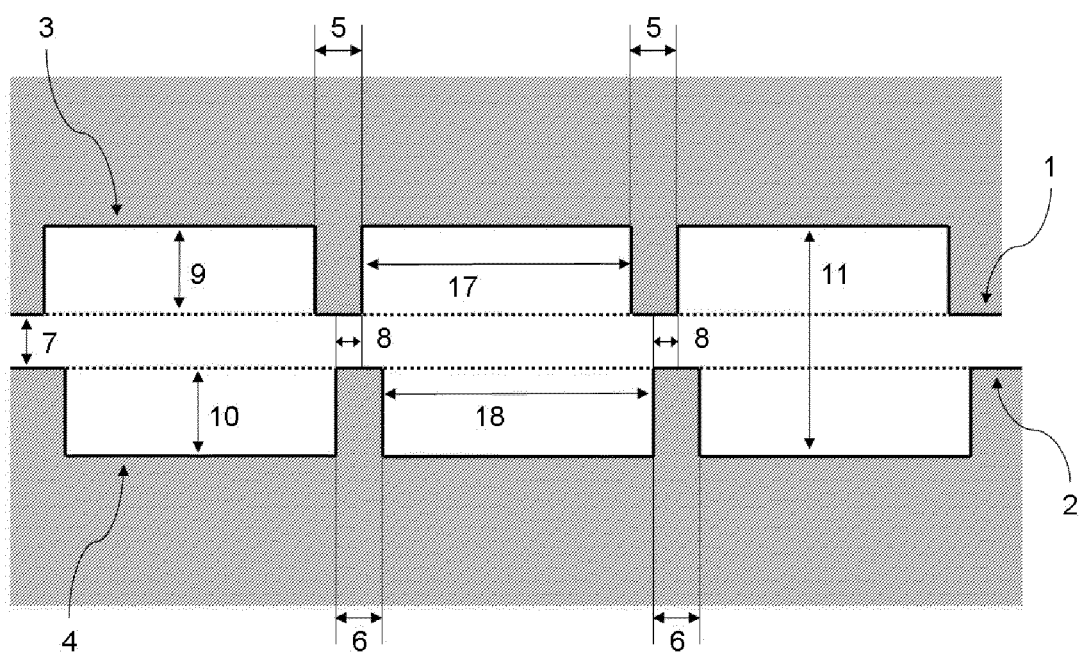
FIG. 10: Schematic representation of a preferred embodiment of the CDDM apparatus, cross-sectional view (direction of bulk flow preferably from left to right).
Figure 11:
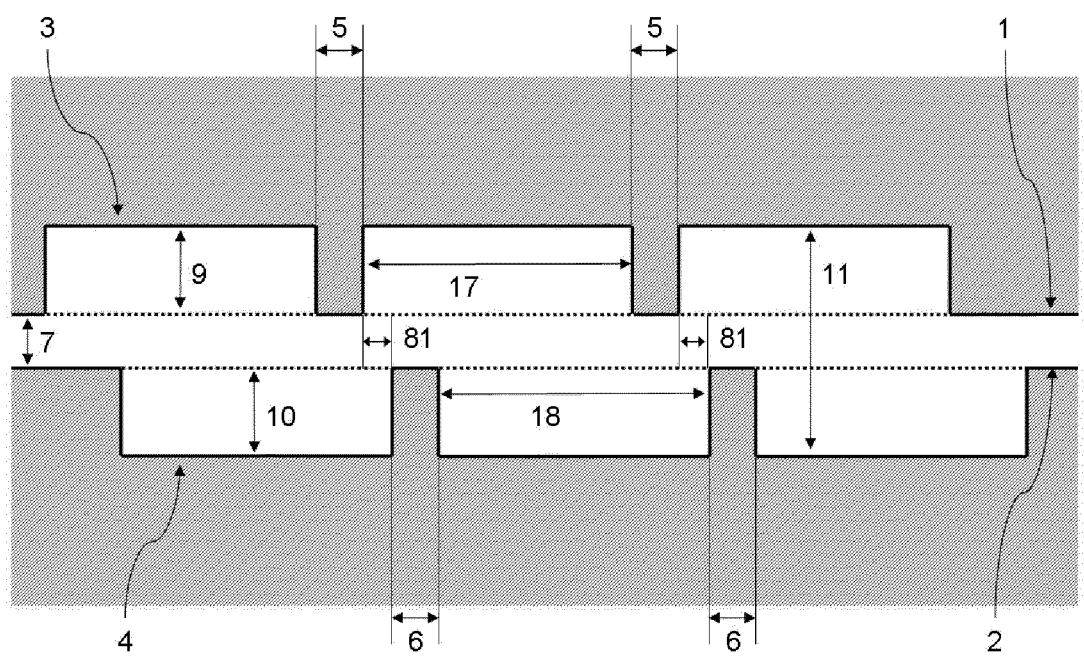
FIG. 11: Schematic representation of a preferred embodiment of the CTM apparatus, cross-sectional view (direction of bulk flow preferably from left to right).

In a preferred embodiment the CDDM apparatus or CTM apparatus can be described by the following. With reference to FIG. 10 and FIG. 11, preferably the CDDM or CTM apparatus comprises two confronting surfaces 1, 2, spaced by a distance 7,
wherein the first surface 1 contains at least three cavities 3, wherein at least one of the cavities has a depth 9 relative to the surface 1,
wherein the second surface 2 contains at least three cavities 4 wherein at least one of the cavities has a depth 10 relative to the surface 2,
wherein the cross-sectional area for flow of the liquid available during passage through the apparatus successively increases and decreases at least 3 times, and
wherein the surface 1 has a length 5 between two cavities, and
wherein the surface 2 has a length 6 between two cavities, and
wherein the surfaces 1, 2 are positioned such that the corresponding lengths 5, 6 overlap to create a slit having a length 8 or do not overlap creating a length 81,
wherein the cavities are arranged such that the cross-sectional area for flow of the liquid available during passage through the apparatus successively increases in the cavities and decreases in the slits by a factor of at least 3, and
wherein the distance 7 between the two surfaces 1,2 is between 2 micrometer and 300 micrometer, and wherein either the ratio between the length 8 and the distance 7 between the two surfaces 1, 2 ranges from 0 to 250,
or wherein the ratio between the length 81 and the distance 7 between the two surfaces 1, 2 ranges from 0 to 30.

With reference to FIG. 10 and FIG. 11: as with the CTM and the CDDM there are several possible configurations for the mixing apparatus. In one preferred combination the confronting surfaces 1, 2 are cylindrical. In such a configuration the apparatus will generally comprise a cylindrical drum and co-axial sleeve. The confronting surfaces 1, 2 will be defined by the outer surface of the drum and the inner surface of the sleeve. However, there are alternative configurations in which the confronting surfaces are circular or disk-shaped. Between these two extremes of configuration are those in which the confronting surfaces are conical or frusto-conical. Non-cylindrical embodiments allow for further variation in the shear in different parts of the flow through the mixer.

The regions where the confronting surfaces 1,2 are most closely spaced are those where the shear rate within the mixer tends to be the highest. The slit 7 between the surfaces between the confronting surfaces 1, 2 forms this region, combined with lengths 8 or 81. High shear contributes to power consumption and heating. This is especially true where the confronting surfaces of the mixer are spaced by a gap of less than around 50 micrometer.

Advantageously, confining the regions of high shear to relatively short regions means that the power consumption and the heating effect can be reduced, especially where in the CTM-like regions the confronting surfaces are spaced apart relatively widely.

Hence the apparatus can be designed such that good mixing is obtained, while keeping the pressure drop over the apparatus as small as possible. The design can be modified by adjusting the dimensions of the various parts of the apparatus, as explained in the following.

The distance 7 between the corresponding surfaces preferably is from 2 micrometers to 300 micrometers, which corresponds to the height of the slit. Preferably the distance 7 is between 3 micrometer and 200 micrometer, preferably between 5 micrometer and 150 micrometer, preferably between 5 micrometer and 100 micrometer, preferably between 5 micrometer and 80 micrometer, preferably between 5 and 60 micrometer, preferably between 5 micrometer and 40 micrometer. More preferably the distance 7 is between 8 micrometer and 40 micrometer, more preferably between 8 micrometer and 30 micrometer, more preferably between 10 micrometer and 30 micrometer, more preferably between 10 micrometer and 25 micrometer, more preferably between 15 micrometer and 25 micrometer.

The actual height of the slit 7 depends on the dimensions of the apparatus and the required flow rate, and the skilled person will know how to design the apparatus such that the shear rates within the apparatus remain relatively constant irrespective of the size of the apparatus.

The surfaces 1 and 2 that each contain at least three cavities 3, 4 create a volume between the surfaces for flow of the two fluids which are mixed. The cavities in the surface effectively increase the surface area available for flow. Due to the presence of the cavities, the small area for flow between the surfaces 1 and 2 can be considered to be a slit having a height 7. The distance 5 between two cavities in surface 1 and distance 6 between two cavities in surface 2 and the relative position of these corresponding parts determine the maximum length of the slit.

Preferably, the two surfaces 1, 2 with cavities 3, 4, that together form the volume for the mixing of the aqueous phase from step a) and the lipophilic phase from step b), are positioned such that the corresponding lengths 5, 6 of the surfaces (that create the slit overlap) create a length 8 of the slit (in the direction of the bulk flow) which is maximally 250 times as large as the distance 7 between the surfaces. Preferably the ratio between the length 8 and the distance 7 between the two surfaces 1, 2 ranges from 0 to 100, preferably 0 to 10, preferably 0 to 5. Alternatively the length 81 is preferably maximally 600 micrometers. Preferably and alternatively the surfaces 1, 2 are positioned such that no overlap is created, however in that case a length 81 is created. The ratio between the length 81 and the distance 7 between the two surfaces 1, 2 preferably ranges from 0 to 30. In that case there is no overlap between the corresponding parts of the surfaces, and the slit is created with what could be called a 'negative overlap'. This 'negative overlap' accommodates the possibility of near zero distance 7 between the two corresponding surfaces 1 and 2. Preferably the length 81 is such, that the ratio between the length 81 and the distance 7 between the two surfaces 1, 2 ranges from 0 to 15, more preferred from 0 to 10, more preferably from 0 to 5 and most preferably from 0 to 2.

A further benefit of this variation in the normal separation of the confronting surfaces in the direction of bulk flow, is that by having relatively small regions of high shear, especially with a low residence time is that the pressure drop along the mixer can be reduced without a compromise in mixing performance.

The little overlap between the corresponding parts of the surfaces 1, 2 leads to a relatively small pressure that is required in order to create a fine dispersion, as compared to apparatuses which have a longer overlap and consequently also need a higher pressure. Usually a longer distance of a slit (or longer capillary) leads to smaller droplets of the dispersed phase. Now we found that with a short capillary or even without capillary the droplets of the dispersed phase remains small, while the pressure required is relative low, as compared to a longer overlap. For example high pressure homogenisers may operates at pressure up to 1,600 bar or even higher. Preferably the mixer according to the invention is operated at a pressure less than 200 bar, preferably less than 80 bar, preferably less than 60 bar, preferably less than 40 bar, most preferred less than 30 bar. With these relatively low pressures a good mixing process is obtained.

An additional advantage of the relatively low pressure is that the energy consumption for applying the pressure is much lower than in conventional devices which use pressures of 1,000 bar or higher to achieve dispersed phases having a size less than 1 micrometer. Moreover less stringent material specifications for design of an apparatus to withstand high pressures is required, such that raw materials can be saved.

With reference to FIG. 10 and FIG. 11, the fluids preferably flow from left to right through the apparatus. The slits create an acceleration of the flow, while at the exit of the slit the fluids decelerate due to the increase of the surface area for flow and the expansion which occurs. The acceleration and deceleration leads to the break up of the large droplets of the dispersed phase, to create finely dispersed droplets in a continuous phase. The droplets which are already small remain relatively untouched. The flow in the cavities is such that the droplets of the dispersed phase eventually become evenly distributed in the continuous phase.

The cross-sectional area for flow of the liquid available during passage through the apparatus successively increases and decreases at least 3 times, and these passages lead to effective mixing of the two fluids. This means that the cross-sectional area for flow of liquid in the cavities is at least 3 times larger than the cross-sectional area for flow of liquid in the slits. This relates to the ratio between lengths 11 and 7.

Preferably the cross-sectional area for flow is designed such that the cross-sectional area for flow of the liquid available during passage through the apparatus successively increases and decreases by a factor of at least 5, preferably at least 10, preferably at least 25, preferably at least 50, up to preferred values of 100 to 400. The cross-sectional surface area for flow of the fluids is determined by the depth 9 of the cavities 3 in the first surface 1 and by the depth 10 of the cavities 4 in the second surface 2. The total cross-sectional area is determined by the length 11 between the bottoms of two corresponding cavities in the opposite surfaces.

The surfaces 1, 2 each contain at least three cavities 3, 4. In that case the flow expands at least 3 times during passage, and the flow passes through at least 3 slits during the passage. Preferably the cross-sectional area for flow of the liquid available during passage through the apparatus successively increases and decreases between 4 and 8 times. This means that the flow during passage experiences the presence of between 4 and 8 slits and cavities.

The shape of the cavities 3 may take any suitable form, for example the cross-section may not be rectangular, but may take the shape of for example a trapezoid, or a parallelogram, or a rectangle where the corners are rounded. Seen from above, the cavities may be rectangular, square, or circular, or any other suitable shape. Any arrangement of the cavities and the number of cavities and size of the cavities may be within the scope of the present invention.

The apparatus may be operated both in static mode (no rotation), as well as dynamic (with rotation). In that case preferably one of the surfaces is able to rotate relative to the other surface at a frequency between 10 and 40,000 rotations per minute, preferably between 20 and 35,000 rotations per minute, more preferably between 1,000 and 25,000 rotations per minute.

In general rotation may lead to improved mixing process and creation of smaller dispersed phase droplets. Static operation has the advantage that less energy is required for mixing. Operation of the device without rotation leads to very efficient and effective mixing of fluids. Without rotation similar dispersed phase sizes can be obtained, without requirement of high pressure or use of energy for rotation. On the other hand rotation at high frequencies may lead to very finely dispersed droplets of the dispersed phase in case two fluids are mixed to create an emulsion.

Additional features of the known CTM and CDDM may be incorporated in the mixer described herein. For example, one or both of the confronting surfaces may be provided with means to heat or cool it. Where cavities are provided in the confronting surfaces these may have a different geometry in different parts of the mixer to as to further vary the shear conditions.

In a preferred example, the dimensions of such a CDDM apparatus used in the invention are such that the distance between the two surfaces 7 is between 10 and 20 micrometer; and/or wherein the length of the slit 8 is maximally 2 millimeter, for example 80 micrometer, or 20 micrometer, or even 0 micrometer. The length of the slit 8 plus the length of the cavity 17, 18 combined is maximally 10 millimeter; and/or wherein the depth of the cavities 9, 10 is maximally 2 millimeter. In that case preferably the internal diameter of the outer surface is between 20 and 30 millimeter, preferably about 25 millimeter. The total length of the apparatus in that case is between 7 and 13 centimeter, preferably about 10 centimeter. The length means that this is the zone where the fluids are mixed. The rotational speed of such a preferred apparatus is preferably 0 (static), or more preferred alternatively between 5,000 and 25,000 rotations per minute.

The shape of the area for liquid flow may take different forms, and naturally depends on the shape of the confronting surfaces. If the surfaces are flat, then the cross-sectional area for flow may be rectangular. The two confronting surfaces may also be in a circular shape, for example a cylindrical rotor which is positioned in the centre of a cylindrical pipe, wherein the outside of the cylindrical rotor forms a surface, and the inner surface of the cylindrical pipe forms the other surface. The circular annulus between the two confronting surface is available for liquid flow.

Emulsion Obtained by the Method According to the Invention

The present invention also provides a water-continuous emulsion obtained by the method according to the invention. Such an emulsion comprises a dispersed phase that comprises a lipophilic compound, wherein the mean Sauter diameter of the dispersed phase is less than 1 micrometer, and wherein the concentration of the dispersed phase is at least 20% by weight of the emulsion.

Preferred aspects disclosed herein before in the context of the invention are also applicable to this further aspect of the invention, mutatis mutandis. Preferably, the lipophilic compound compound comprises lecithin, fatty acid, monoglyceride, diglyceride, triglyceride, phytosterol, phytostanol, phytosteryl-fatty acid ester, phytostanyl-fatty acid ester, wax, fatty alcohol, carotenoid, oil-soluble colourant, oil-soluble vitamin, oil soluble flavour, oil soluble fragrance, mineral oils or derivatives, petrolatum or derivatives, or silicon oils or derivatives, or combinations of these compounds. More preferred the lipophilic compound is selected from the group of phytosterols, carotenoids, and derivatives of these compounds. Also mixtures of these compounds are within the scope of the invention.

Preferably the lipophilic compound is mixed with a non-aqueous phase, which together form the dispersed phase of the emulsion. Preferably the non-aqueous phase comprises a vegetable oil, for example sunflower oil, palm oil, olive oil, rapeseed oil, or any other suitable oil or combinations of oils. The oil may be liquid at room temperature, or alternatively may be solid at room temperature, in which case the oil should be melted first by increasing the temperature. A fat or oil from animal origin, such as fish oil, dairy fat, lard, or tallow, may be used as well. Such a vegetable or animal oil obtained from step b) may be used as an ingredient of food products.

The optional non-aqueous phase may also be chosen from materials like mineral oils, petrolatum, and silicon oils, and derivatives of these compounds, and combinations of these. Preferably the concentration of the lipophilic compound in the non-aqueous phase is at least 5% by weight, preferably at least 10% by weight, preferably at least 20% by weight.

The mean Sauter diameter of the dispersed phase is less than 1 micrometer, preferably less than 500 nanometer. Even more preferred the mean Sauter diameter of the dispersed phase is less than 400 nanometer, more preferred less than 300 nanometer.

The concentration of dispersed phase in the emulsion that is obtained from step c) is at least 20% by weight of the emulsion. Preferably the concentration of the dispersed phase is at least 40% by weight of the emulsion, preferably at least 50% of the emulsion. Preferably the dispersed phase comprises at least 60% by weight of the emulsion.

Mostly preferred the water-continuous emulsion obtained by the method according to the invention comprises a dispersed phase that comprises a phytosterol, wherein the mean Sauter diameter of the dispersed phase is less than 1 micrometer, and wherein the concentration of the dispersed phase is at least 20% by weight of the emulsion. Preferably the phytosterol is dispersed in a non-aqueous phase. Preferably the non-aqueous phase comprises a vegetable oil, for example sunflower oil, palm oil, olive oil, rapeseed oil, or any other suitable oil or combinations of oils. fat or oil from animal origin, such as fish oil, dairy fat, lard, or tallow, may be used as well. Preferably the concentration of the phytosterol in the non-aqueous phase is at least 5% by weight, preferably at least 10% by weight, preferably at least 20% by weight. Preferably the mean Sauter diameter of the dispersed phase is less than 500 nanometer, preferably less than 400 nanometer, more preferred less than 300 nanometer. Preferably the concentration of the dispersed phase is at least 40% by weight of the emulsion, preferably at least 60% of the emulsion. Preferably the total concentration of the phytosterol based on the weight of the emulsion is between 5 and 20% by weight of the emulsion.

The present invention also provides a food product or a personal care product or a home care product or a cosmetic product, or a pharmaceutical product comprising the emulsion according to the first aspect of the invention. The emulsion obtained by the method according to the invention may be used as such or as ingredient of food products such as water-in-oil emulsions or oil-in-water emulsions, or personal care products, such as skin creams, or as ingredient in home care products, such as liquid laundry detergents. These personal care products may be oil-in-water emulsions. Also double emulsions and multiple emulsions (like oil-in-water-in-oil and water-in-oil-in-water emulsions) are emulsions which are within the scope of the present invention. For example the water-continuous emulsion can be used to create an oil-in-water-in-oil emulsion: the water-continuous emulsion obtained from step c) of the method according to the invention can be emulsified in a continuous oil phase.

In the case of food products, the non-aqueous phase can be a lipid phase, for example droplets of a dairy fat or sunflower oil dispersed in an aqueous phase to form an oil-in-water emulsion. Examples of oil-in-water emulsions are dressings and mayonnaise-type products, dairy spreads, and body lotions and skin creams. Also dairy drinks such as drink yoghurt or milk, are oil-in-water emulsions, if they are not fat-free. In case of water-in-oil emulsion such as margarines, butter, and other spreads, the lipid phase can be considered to be the continuous vegetable oil phase or butter fat phase, as applicable.

In case of personal care products or home care products, the non-aqueous phase may be chosen from materials like mineral oils, petrolatum, and silicon oils, and derivatives of these compounds, and combinations of these.

The amount of non-aqueous phase in such products may range from 1% by weight to 99% by weight of the product, depending on the product. For example a shortening may contain 99% by weight of edible oil or fat. A margarine contains about 80% edible oils and fats. A water-in-oil spread may contain from 20 to 70% by weight of edible oils and fats. A dressing or mayonnaise may contain from about 5% by weight up to 80% by weight of non-aqueous lipid phase. A dairy spread may contain about 20 to 30% by weight of edible oils and fats. A dairy drink or the like may contain up to 5% by weight of edible oils and fats. A skin cream may contain about 5 to 20% by weight of lipophilic compounds.

Additionally preferably the present invention provides a food product comprising the emulsion prepared according to the method of the invention. Such a product may be produced using any conventional production method, by bringing the obtained water-continuous emulsion into contact with one or more other ingredients of such a product. Subsequently the normal preparation process for such a product can be carried out.

The food products of the invention may be all kinds of food products, for instance marinades, sauces, seasonings, butter, spray products, spreads, liquid shallow frying products, seasonings, dressings, mayonnaise, low-fat mayonnaise, and ice cream.

Preferably, food products according to the invention are spreads (water-in-oil emulsions or oil-in-water emulsions), margarines (water-in-oil emulsions), dairy products such as butter (water-in-oil emulsion), or liquid water-in-oil emulsions or liquid oil-in-water emulsions designed for shallow frying.

Other preferred food products according to the invention are beverages containing the emulsion obtained from the method according to the invention. An advantage of the emulsions prepared according to the present invention is that transparent beverages can be produced, because of the small size of the dispersed phase droplets, which are preferably smaller than the wavelength of visible light.

Additionally preferably the present invention provides a personal care product comprising the emulsion prepared according to the method of the first aspect of the invention. In this case the personal care product is for example a skin cream, a body lotion, bodywash, handwash, facial foam, shampoo, or hair conditioner.

Additionally preferably the present invention provides a home care product comprising the emulsion prepared according to the method of the first aspect of the invention. In this case the home care product is for example a laundry detergent composition, preferably a liquid laundry detergent composition, or a laundry conditioner composition.

Additionally preferably the present invention provides a cosmetic product comprising the emulsion prepared according to the method of the first aspect of the invention. In this case the cosmetic product is for example make-up like lipstick, eye and lip products.

Additionally preferably the present invention provides a pharmaceutical product comprising the emulsion prepared according to the method of the first aspect of the invention. In this case the pharmaceutical product is for example a composition wherein drugs have been encapsulated in a non-aqueous phase for targeted delivery in vivo.

The various features and embodiments of the present invention, referred to in individual sections below apply, as appropriate, to other sections, mutatis mutandis. Consequently features specified in one section may be combined with features specified in other sections, as appropriate. All publications mentioned in this specification are herein incorporated by reference. Various modifications and variations of the described methods and products of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the relevant fields are intended to be within the scope of the claims.

EXAMPLES

The following non-limiting examples illustrate the present invention.

CDDM Apparatus

The experiments were carried out in a CDDM apparatus as schematically depicted in FIG. 2 and FIG. 10, wherein the apparatus comprises a cylindrical drum and co-axial sleeve (the confronting surfaces 1, 2 are cylindrical). The confronting surfaces 1, 2 are defined by the outer surface of the drum and the inner surface of the sleeve, respectively. The CDDM can be described by the following parameters:
  slit height 7 is 10 micrometer,
  slit length 8 is 120 micrometer;
  total length of the apparatus is 10 centimeter (length means the zone where the fluids are mixed);
  across the length of the CDDM in axial direction (in flow direction) the flow experiences six slits with height 7, the flow is contracted 6 times;
  depth of cavities 3, 4 is maximally 2 millimeter;
  internal diameter of the stator is 25 millimeter;
  rotational speed of the apparatus is up to 25,000 rotations per minute, and it was operated in these experiments at maximally 18,000 rotations per minute.

Particle Size Distribution

Particle sizes and their distribution were determined using static and dynamic light scattering (SLS and DLS respectively) with instruments Mastersizer 2000 and Zetasizer Nano series ZS (Malvern Instruments, UK). The dispersions made were first diluted using deionised water (approximately 100 folds). SLS technique was used to compare the measurement done by DLS technique and also to check the presence of bigger particles which are beyond the DLS detection range. Sauter mean diameter ($d_{3,2}$), $d_{4,3}$ and Span were determined using SLS.

Scanning Electron Microscopy (SEM)

Low temperature field emission scanning electron microscopy was used. One drop of dispersion was mounted onto a 1 mm internal diameter brass rivet and plunged into nitrogen slush. After transfer to a Gatan Alto 2500 cryoplunger, low temperature preparation chamber samples were fractured at −98° C., etched for 15 seconds, cooled to −110° C. and coated with 2 nm Pt/Pd. Examination was carried out using a JEOL 6301F scanning electron microscope fitted with a Gatan cold stage at −150° C. operated at 5 KV.

Example 1

Preparation of Highly Concentrated Sterol-Loaded Colloidal Dispersions Using CDDM Apparatus Myritol® 318 (Medium chain triglyceride (MCT) oil, from Cognis, Monheim am Rhein, Germany) and a crystalline phytosterol blend (containing 84% beta-sitosterol, 7%, phytostanols, 9% other sterols, from Cognis, Monheim am Rhein, Germany) were used as the dispersed phase material. A non-ionic emulsifier polyoxyethylene (20) sorbitan monolaurate, commercially known as Tween®20, was bought from Sigma Aldrich (UK). Phospholipon 80 was supplied by Phospholipid GmbH (Cologne, Germany).

Phytosterol-loaded colloidal dispersions were prepared in ratios of dispersed phase:continuous phase of 70:30 and 65:35 (w/w). The dispersed phase was prepared with two different concentrations of phytosterol in MCT oil and phospholipon 80, corresponding to phytosterol concentrations were 7% and 13% (w/w) based on the total colloidal dispersion. The percentage of emulsifier Tween 20 varied from 7% to 9%. Phospholipon was added as crystallization inhibitor at 1.7% (w/w), based on the weight of the total dispersion.

For the production of all colloidal dispersions the disperse phase, a solution of phytosterol and phospholipon in MCT-oil, and the continuous phase, water and Tween 20, were separately heated up to 108° C. and 90° C., respectively. The dispersed phase was continuously stirred in a feed hopper using a rotor-stator system (Fluid Division Mixing). The continuous phase was prepared by heating water with Tween 20 at 90° C. with continuous stirring using a magnetic stirrer.

Oil-in-water (O/W) colloidal dispersions containing sterols were produced in line using the CDDM apparatus described herein before. The experiments were carried out by the CDDM across a range of flow rates from 20 mL/s to 84 mL/s, and rotational speeds from 0 rpm (static mode) to 18,000 rpm (dynamic mode). In each experiment, 50 g dispersions were prepared with final temperatures between 55° C. and 70° C. Afterwards, samples were left on the bench for cooling until they reached room temperature.

After collecting the hot samples, their droplet size and size distributions were measured by static light scattering (SLS). After cooling their morphology were analysed by scanning electronic microscopy (SEM), in order to determine whether the phytosterols had remained in the dispersed phase or had crystallized at the oil-water interface and thereby migrated to the continuous phase during the process/after cooling down.

Colloidal Dispersions Containing 7% Phytosterol

The CDDM apparatus was operated at flow rates in the range of 20 to 80 mL/s and rotor speeds from 0 to 18,000 rpm. The pressure drop was in the order of 40 to 80 bar. The droplet size distribution of the phytosterols dispersed in MCT oil was determined by static light scattering (see FIG. 3 and Table 1), and this showed that all rotational speeds dynamic process provides narrower droplet size distribution, consequently less polydispersity than the static one. Higher speeds may provide a bigger impact on droplet size distribution, as can be seen at 15,000 rpm, which droplets are monodisperse. At higher speeds, emulsifier molecules may quickly reach an interface and it is immediately adsorbed.

TABLE 1

Dispersed phase diameters $d_{3,2}$ and $d_{4,3}$ (in micrometer) and Span; 7% phytosterol dispersion in emulsion, flow rate of 20 mL/s in CDDM, at various rotational speeds.

| rotational speed [rpm] | $d_{3,2}$ [micrometer] | $d_{4,3}$ [micrometer] | Span [—] |
|---|---|---|---|
| 0 | 1.4 | 5.67 | 5.82 |
| 5,000 | 0.81 | 2.51 | 2.08 |
| 8,000 | 0.42 | 0.65 | 1.41 |
| 12,000 | 0.31 | 0.41 | 1.5 |
| 15,000 | 0.31 | 0.42 | 1.5 |

Figure 4:
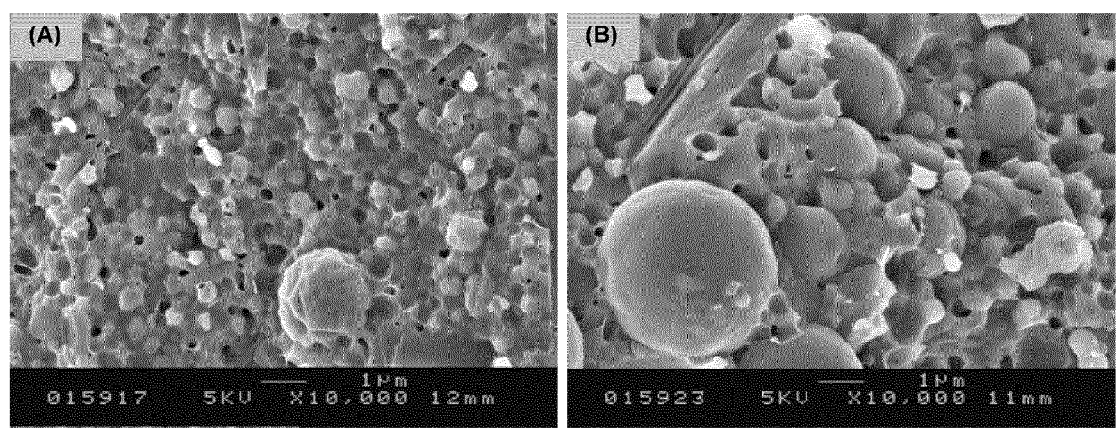
FIG. 4: Scanning electronmiscroscopy images of two 7% phytosterol loaded colloidal dispersions (containing 70% dispersed phase); from example 1.
Image A left: flow rate 22.9 mL/s, speed 8,250 rpm; image width about 12 micrometer, bar width 1 micrometer.
Image B right: flow rate 67.6 mL/s, speed 0 rpm (static); image width about 12 micrometer, bar width 1 micrometer.

Dynamic process has proven that smaller droplets and less phytosterol crystals can be obtained, as can be observed the morphology of colloidal dispersions produced by either dynamic or static processes (FIG. 4). This method allows the production of smaller monodispersed droplets containing phytosterol in amorphous form. It is the most physical stable form of those colloidal dispersions suitable for long shelf-life food products. The amorphous form can be proven by the absence of needles of phytosterols, in spite of the high concentration of phytosterols in the oil. In the case of nano-dispersions as obtained here, droplet size provides a further positive result on the prevention of phytosterol crystallisation.

Figure 5:
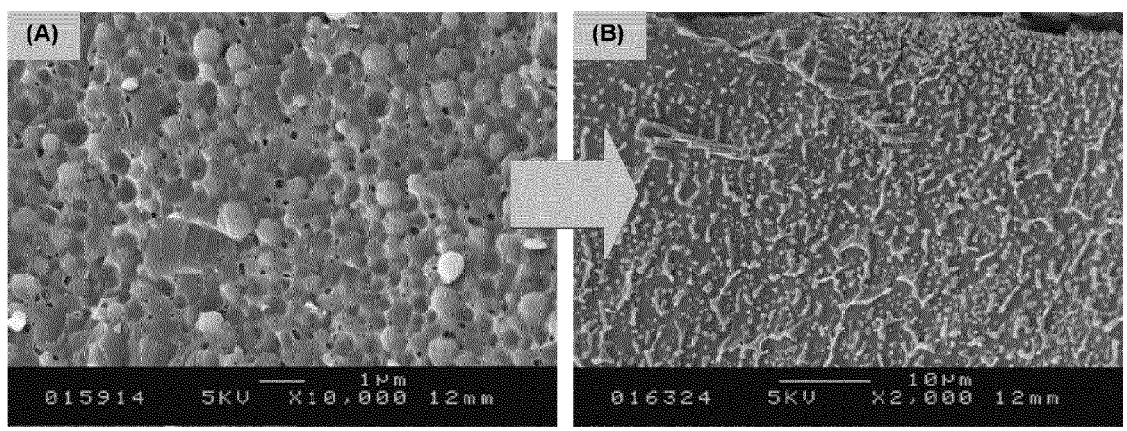
FIG. 5: Scanning electronmiscroscopy images of phytosterol loaded colloidal dispersions; from example 1; CDDM at flow rate 22.9 mL/s, speed 8,250 rpm.
Image A left: 70% dispersed phase, 7 wt % phytosterol based on dispersion; image width about 12 micrometer, bar width 1 micrometer.
Image B right: dispersion from image A diluted to 10% dispersed phase; 1 wt % phytosterol based on dispersion; image width about 60 micrometer, bar width 10 micrometer.
Figure 6:
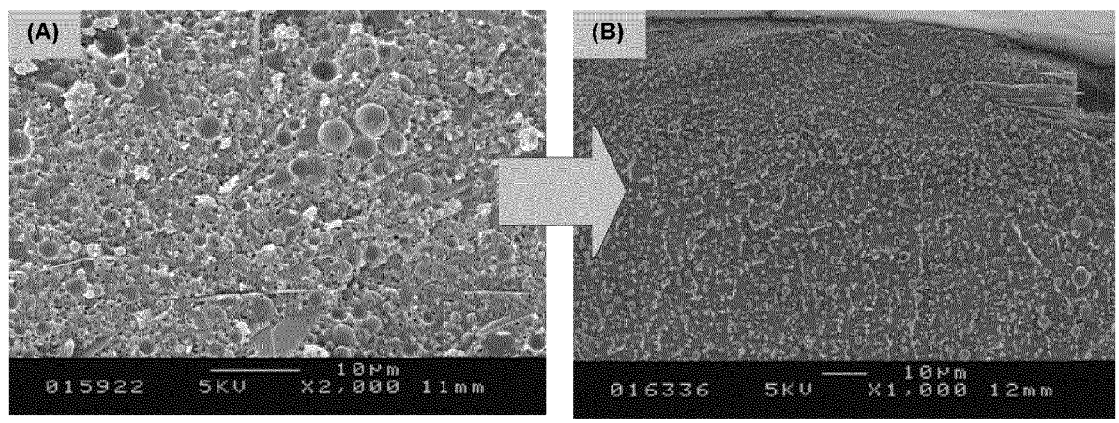
FIG. 6: Scanning electronmiscroscopy images of phytosterol loaded colloidal dispersions (containing 70% dispersed phase); from example 1; CDDM at flow rate 22.9 mL/s, speed 0 rpm (static).
Image A left: 70% dispersed phase, 7 wt % phytosterol based on dispersion; image width about 60 micrometer, bar width 10 micrometer.
Image B right: dispersion from image A diluted to 10% dispersed phase; 1 wt % phytosterol based on dispersion; image width about 60 micrometer, bar width 10 micrometer.

FIG. 5 and FIG. 6 show the morphology of 7% phytosterol-loaded colloidal dispersions (concentrated 70/30 and diluted 10/90) produced by dynamic and static processes respectively. After dilution, particle morphologies show liquid droplets, which may be characterised as undercooled emulsion.

Figure 7:
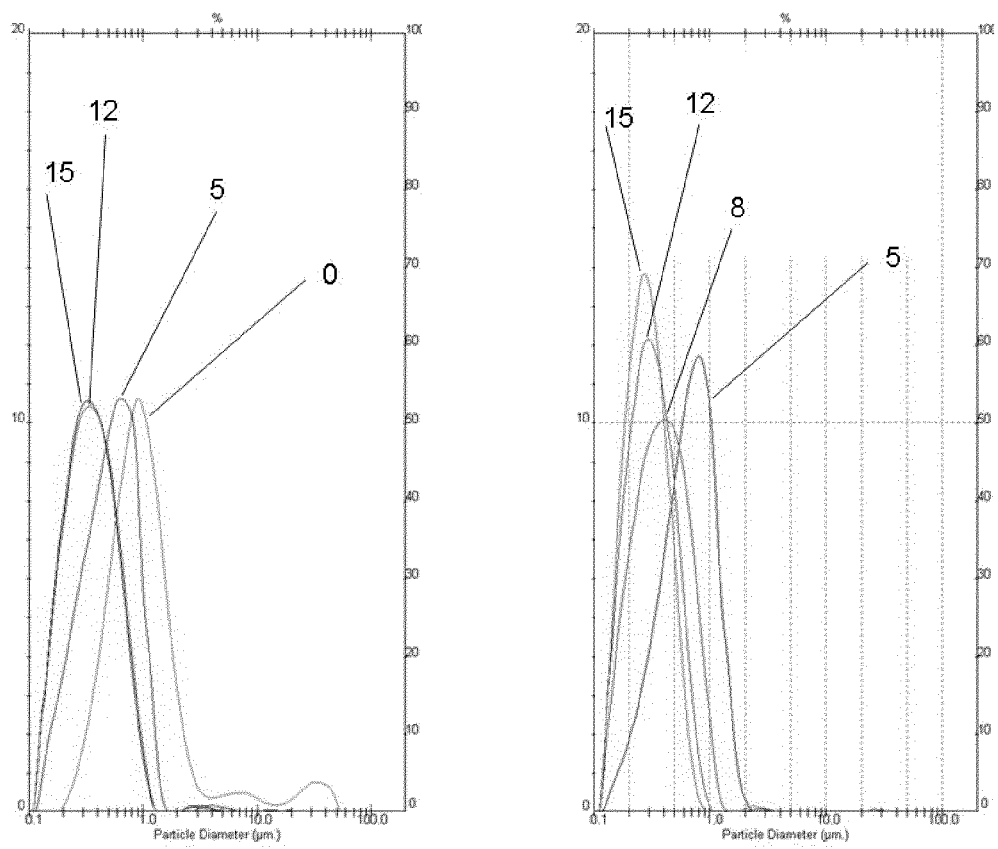
FIG. 7: Droplet size distribution of 7 wt % phytosterol-loaded colloidal dispersions stabilized by Tween 20 at two different concentrations, produced at CDDM flow rate 20 mL/s; static and dynamic processes; from example 1; (0=0 rpm, 5=5,000 rpm, 8=8,000 rpm, 12=12,000 rpm, 15=15,000 rpm); image left 7 wt % Tween 20, and image right 9 wt % Tween 20.

FIG. 7 compares the droplet size distributions of 7% phytosterol-loaded colloidal dispersions stabilized by Tween® 20 at concentrations of 7% and 9%. It was observed that increase of emulsifier concentration provides smaller droplets (more surface area) (Table 2) and narrower droplet size distribution, protecting droplets against coalescence and Ostwald ripening.

TABLE 2

Dispersed phase diameters $d_{3,2}$ and $d_{4,3}$ and Span of 7 wt % phytosterol dispersion, flow rate of 20 mL/s in CDDM, at various rotational speeds, and at two Tween 20 concentrations in the dispersion.

| rotational speed [rpm] | Concentration Tween 20: 7 wt % | | | concentration Tween 20: 9 wt % | | |
|---|---|---|---|---|---|---|
| | $d_{3,2}$ [micron] | $d_{4,3}$ [micron] | Span [—] | $d_{3,2}$ [micron] | $d_{4,3}$ [micron] | Span [—] |
| 0 | 1.4 | 5.7 | 5.8 | 1.4 | 6.9 | 6.8 |
| 5,000 | 0.9 | 2.5 | 2.1 | 0.6 | 0.8 | 1.3 |
| 8,000 | 0.5 | 0.7 | 1.4 | 0.4 | 0.5 | 1.5 |
| 12,000 | 0.4 | 0.5 | 1.5 | 0.3 | 0.5 | 1.3 |
| 15,000 | 0.4 | 0.5 | 1.5 | 0.3 | 0.4 | 1.1 |

Higher speeds provide more energy dissipation through the emulsification process and smaller monodisperse droplets can be produced, which is shown in Table 3.

TABLE 3

Dispersed phase diameters $d_{3,2}$ and $d_{4,3}$ (in micrometer) and Span; 7% phytosterol dispersion, in CDDM at 18,000 rpm, various flow rates.

| flow rate [mL/s] | $d_{3,2}$ [micrometer] | $d_{4,3}$ [micrometer] | Span |
|---|---|---|---|
| 20 | 0.26 | 0.77 | 1.18 |
| 40 | 0.27 | 0.32 | 1.16 |
| 80 | 0.29 | 0.37 | 1.40 |

The influence of the flow rate on $d_{3,2}$ was not very large in this experiment, while some effect on $d_{4,3}$ was shown.

Sauter mean diameters ($d_{3,2}$) of the dispersions were between 260 and 290 nanometer After running at 18,000 rpm and 40 mL/s, a semi-transparent emulsion was produced.

Colloidal Dispersions Containing 13% Phytosterol

High concentration of phytosterol could be successfully incorporated into fine oil droplets. In this kind of formulation, the active molecule is in a supersaturated oil solution, where the volume of each single droplet is further reduced during processing. Increase in surface area provides a reduction in number of crystal nuclei per droplet, consequently the chance of crystal nuclei to reach each other is reduced and crystallisation can barely occurs.

Figure 8:
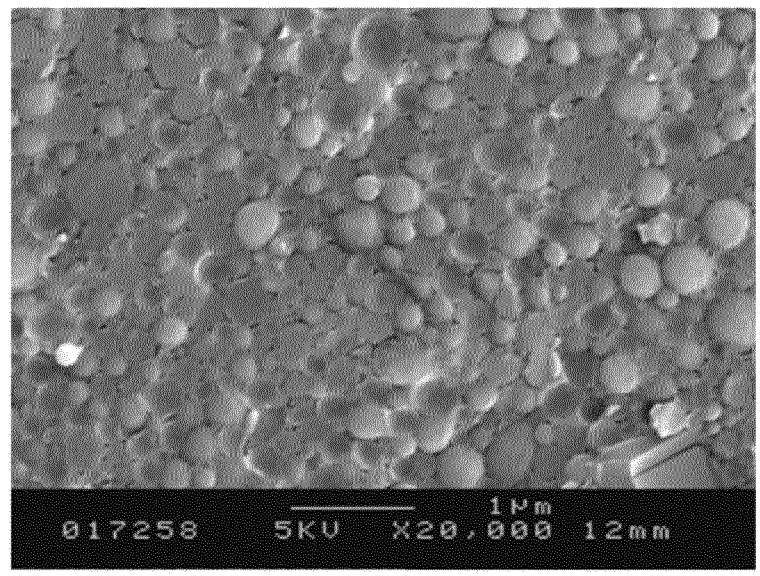
FIG. 8: Scanning electronmiscroscopy image of 13 wt % phytosterol loaded colloidal dispersion (containing 65% dispersed phase); produced in CDDM at flow rate of 80 mL/s and 12,000 rpm; from example 1; image width about 6 micrometer (bar width 1 micrometer).

FIG. 8 shows a SEM image of a sample prepared at 80 mL/s and 12,000 rpm. Disperse and continuous phase were 65 wt % and 35 wt % respectively, with phytosterol concentration of about 20% in the dispersed phase, leading to a phytosterol concentration of about 13 wt % in the dispersion. The $d_{3,2}$ and $d_{4,3}$ were 290 and 500 nanometer, respectively, and span was 1.44.

A similar sample (disperse and continuous phase were 65 wt % and 35 wt % respectively, with phytosterol concentration of about 20% in the dispersed phase, leading to a phytosterol concentration of about 13 wt % in the dispersion) was made at a flow rate of 40 mL/s and 12,000 rpm. The $d_{3,2}$ of the dispersed phase was about 320 nanometer.

Figure 3:
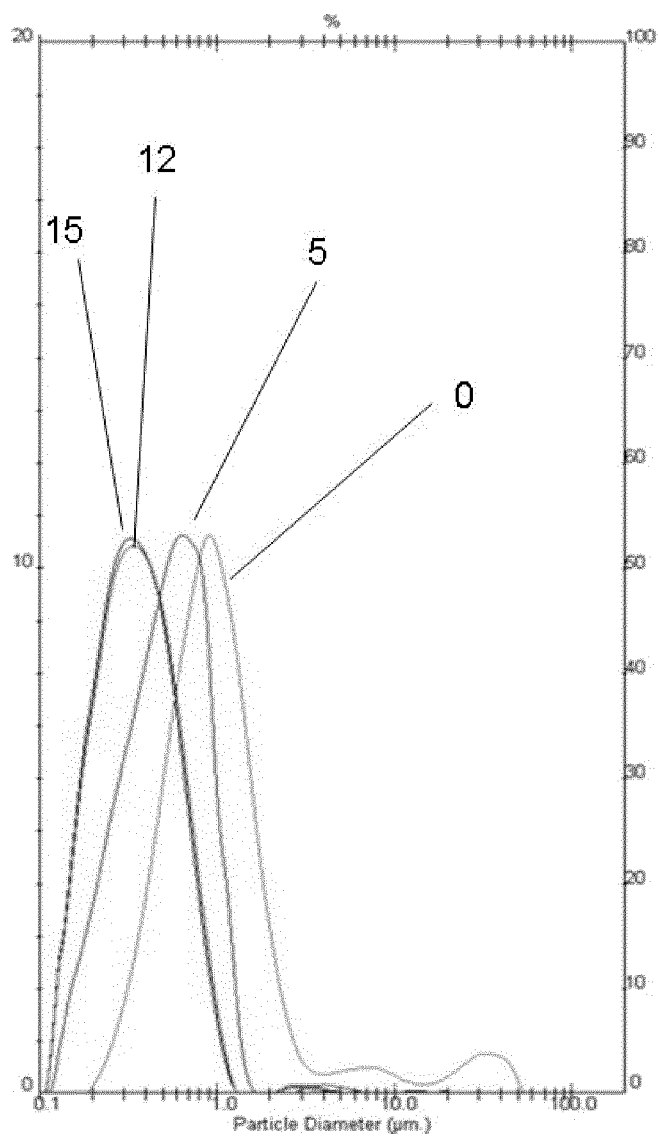
FIG. 3: Particle size distribution of 7% phytosterol droplets dispersed in MCT oil, from example 1; at flow rate of 20 mL/s in CDDM, at various rotational speeds (0=0 rpm, 5=5,000 rpm, 12=12,000 rpm, 15=15,000 rpm).

FIG. 3.9 illustrates the droplet size distribution and SEM image of two samples prepared at 40 mL/s and different rotational speeds. Disperse and continuous phase were also 65% and 35% respectively, with phytosterol concentration of 7% and 13%. Smaller droplets and narrower droplet size distribution were obtained at higher speed, even at higher phytosterol concentration.

This example 1 relates to a method for the control of the crystal habit of species via the manufacture of concentrated sub micron emulsions.

Comparative Example 2

Preparation of Sterol-Loaded Colloidal Dispersions Using High Pressure Homogeniser The same raw materials as in example 1 were used, and additionally solid glyceryl tridodecanoate (trilaurin, ex Fluka, melting point of 46.5° C. was obtained from Sigma Aldrich (UK). Oil-in-water (O/W) colloidal dispersions were prepared using a high pressure homogeniser, the Microfluidizer M-110S (Microfluidics Internationalional Corporation, MA-Newton, USA). It consists of the following major components: air motor, intensifier pump, and interaction chamber. It can be operated within the pressure range of about 200 to 1,600 bar and a flow rate range of about 250 to 600 mL/min (about 4 to 10 mL/s). The ratio of dispersed phase to continuous phase was 10 to 90 (w/w). In the continuous phase the percentage of emulsifier Tween 20 varied from 1% to 4% and water from 86% to 89%. The dispersed phase (10%) was prepared with variable levels of phytosterol in either MCT oil or trilaurin. Phytosterol ranged from 1 wt % to 4 wt % based on the total colloidal dispersion which is equivalent to 10 wt % to 40 wt % of the dispersed phase.

The dispersions were prepared by heating MCT oil or trilaurin with phytosterol to about 100° C. The continuous phase (90%) was prepared by heating deionised water with Tween 20 at 90° C. with continuous stirring using a magnetic stirrer. The continuous phase was placed in the sample unit of the Microfluidizer, which was pre-heated to 95° C. using a water bath, and then the disperse phase was added. A coarse emulsion was prepared using a rotor stator system (Ultra Turrax IKA T-25 digital; IKA Werke GmbH & Co. KG, Staufen, Germany), adapted with a helix at a speed of 450 rpm. This was then further processed at the Microfluidizer, applying 4 homogenisation cycles at 1165 bar at 90° C. to prepare the colloidal dispersion loaded with phytosterol. This was then left unstirred to cool at ambient conditions to 20° C. (about 1° C./min). The flow rate was 3 to 4 mL/s.

Results on particle diameter (as measured using DLS) are the following, as function of phytosterol concentration and of oil phase.

TABLE 4

Dispersed phase diameters $d_{3,2}$ and $d_{4,3}$ (in micrometer) and Span; 7% phytosterol dispersion, in Microfluidizer at 1165 bar and 90° C.

| oil phase [wt % of emulsion] | concentration phytosterol [wt % of emulsion] | $d_{3,2}$ [micrometer] |
|---|---|---|
| MCT oil 9% | 1 | 0.22 |
| MCT oil 8% | 2 | 0.19 |

TABLE 4-continued

Dispersed phase diameters $d_{3,2}$ and $d_{4,3}$ (in micrometer) and Span; 7% phytosterol dispersion, in Microfluidizer at 1165 bar and 90° C.

| oil phase [wt % of emulsion] | concentration phytosterol [wt % of emulsion] | $d_{3,2}$ [micrometer] |
|---|---|---|
| trilaurin 9% | 1 | 0.19 |
| trilaurin 8% | 2 | 0.19 |

Figure 9:
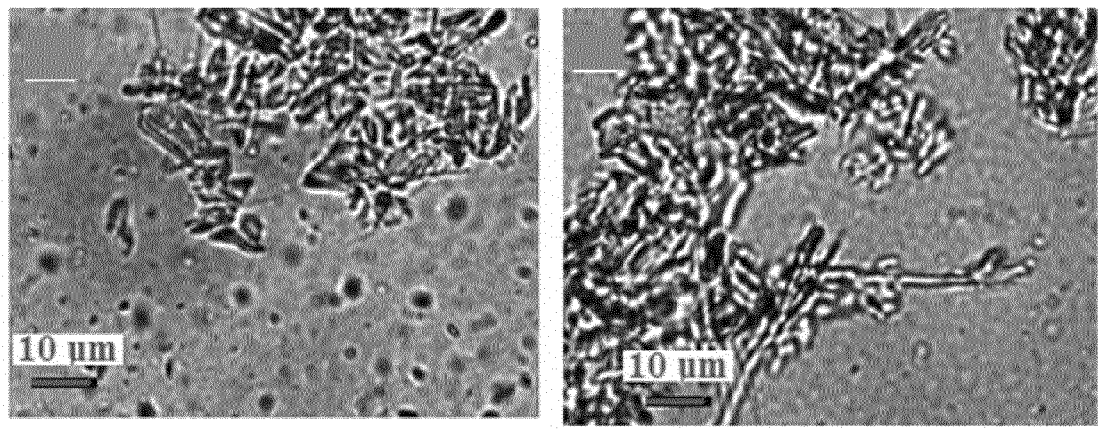
FIG. 9: Light microscopy images of dispersions containing 7 wt % MCT oil and 3 wt % phytosterol (left) or 6 wt % MCT oil and 4 wt % phytosterol (right), bar width 10 micrometer; from example 2.

Also dispersions containing higher concentrations of phytosterol were prepared, 3 wt % and 4 wt % based on the weight of the emulsion. Microscopy images revealed that dispersions containing 7 wt % MCT oil and 3 wt % phytosterol or 6 wt % MCT oil and 4 wt % phytosterol, respectively, contained the phytosterols in the form of needles (see FIG. 9). The length of these needles was up to tens of micrometers. This effect was particularly pronounced at the higher phytosterol concentrations.

This example 2 relates to a method for the production of solid micro-encapsulates or carriers via the manufacture of sub-micron emulsions.

Comparing the CDDM apparatus to the Microfluidizer shows that the CDDM-produced material had a final dispersed phase fraction about 6 to 7 times higher, and up to a 30-fold lower pressure drop than the Microfluidizer. Moreover the phytosterol dispersions produced using the CDDM apparatus also kept a small dispersed particle size, meaning that the sterols did not crystallise and remained in an amorphous state.

Example 3

Preparation of Highly Concentrated Silicone Wax-Loaded Colloidal Dispersions Using CDDM Apparatus Emulsions were made using the CDDM, containing as dispersed phase silicone wax (SilCare 41M65, which is stearyl dimethicone, ex Clariant, UK; melting point 32° C.). The polymer PET-POET (polyethylene terephthalate-co-polyoxyethylene terephthalate, prepared in house as described in WO 2010/105922 A1) was used as emulsifier. Additionally polyoxyethylene (20) sorbitan monolaurate emulsifier (Tween®20, ex Sigma Aldrich, UK) was used as a standard control emulsifier.

These particles comprising a waxy solid and the polymeric deposition aid, which is partially embedded in the waxy solid, may be used in laundry treatment compositions to improve the softening effect on the fabric after washing (as described in WO 2010/105922 A1).

Standard method to produce emulsions of the silicone wax was the following. First, silicone wax was melted to about 20° C. above its melting point. An aqueous phase containing PET-POET or Tween 20 was heated to a temperature of maximally 90° C. Pre-heated continuous and disperse phases were placed in and maintained at 90° C. in feed hoppers for the CDDM apparatus. Homogenisation of the disperse and continuous phases was carried out using the CDDM in line at different flow rates and rotational speeds. The amount of dispersed phase in the emulsions was 65% by weight, and the aqueous phase amounted to 35% by weight. The percentage of emulsifier Tween 20 and PET-POET were 13% and 9% respectively, based on the total emulsion. After using the CDDM, samples were collected at 50° C. and left on the bench for cooling until they reached room temperature.

Silicone Wax Dispersions Stabilised by Tween 20

Silicone wax (60 wt %) colloidal dispersions in water (27 wt %) were made, stabilised by Tween 20 (13 wt %). The results of $d_{3,2}$, $d_{4,3}$, span, and pressure drop over the CDDM apparatus are given in the following table.

TABLE 5

Droplet size distributions of silicone wax colloidal dispersions stabilised by Tween ® 20 and produced by the CDDM apparatus at about 70 mL/s, as function of rotational speed.

| rotational speed [rpm] | flow rate [mL/s] | pressure [bar] | $d_{3,2}$ [micrometer] | $d_{4,3}$ [micrometer] | Span |
|---|---|---|---|---|---|
| 4,000 | 74 | 46 | 0.76 | 0.91 | 1.1 |
| 5,000 | 73 | 49 | 0.66 | 0.80 | 1.1 |
| 6,000 | 73 | 46 | 0.56 | 0.70 | 1.1 |
| 7,000 | 72 | 49 | 0.44 | 0.58 | 1.3 |
| 8,000 | 72 | 46 | 0.39 | 0.51 | 1.4 |
| 10,000 | 73 | 49 | 0.32 | 0.42 | 1.5 |
| 12,500 | 72 | 49 | 0.29 | 0.36 | 1.4 |
| 15,000 | 73 | 49 | 0.28 | 0.36 | 1.4 |

With an increase in rotational speed at constant flow rate (about 70 mL/s), mean Sauter diameter and $d_{4,3}$ decreased. On the other hand SPAN slightly increased at the same process parameters. The smallest $d_{3,2}$ reached was 280 nanometer. This behaviour was observed in all silicone wax dispersions stabilised by Tween® 20. Increase in speed provides more energy transfer efficiency, consequently better dispersive and distribute mixing, leading to a more intensive drop deformation and break up, and faster stabilisation of the emulsifier on the wax/water interface.

Silicone Wax Dispersions Stabilised by PET-POET

Silicone wax (60 wt %) colloidal dispersions in water (31 wt %) were made, stabilised by PET-POET (9 wt %). The results of $d_{3,2}$, $d_{4,3}$, span, and pressure drop over the CDDM apparatus are given in the following table.

TABLE 6

Droplet size distributions of silicone wax colloidal dispersions stabilised by Tween ® 20 and produced by the CDDM apparatus at about 70 mL/s, as function of rotational speed.

| rotational speed [rpm] | flow rate [mL/s] | pressure [bar] | $d_{3,2}$ [micrometer] | $d_{4,3}$ [micrometer] | Span |
|---|---|---|---|---|---|
| 4,000 | 72 | 39 | 2.09 | 5.35 | 1.9 |
| 6,000 | 73 | 39 | 1.46 | 3.49 | 1.8 |
| 8,000 | 73 | 39 | 1.25 | 2.78 | 1.7 |
| 10,000 | 72 | 41 | 0.83 | 1.57 | 1.6 |
| 12,500 | 74 | 41 | 1.03 | 1.43 | 1.4 |
| 15,000 | 72 | 41 | 0.96 | 1.27 | 1.3 |
| 19,000 | 71 | 41 | 2.11 | 9.71 | 4.3 |

This experiment shows that dispersion containing 60 wt % silicon wax can be produced, and wherein the Sauter mean diameter is less than 1 micrometer. Comparing PET-POET to Tween 20 yields that increasing in rotational speed has shown a similar behaviour up to 10,000 rpm at constant flow rate of 70 mL/s. At speeds above 10 k rpm, particle sizes started to increase and also their size distribution increased. This phenomenon may be attributed to the so-called "bridging flocculation" of the particles, where the long chain polymer molecules are adsorbed to the particle surfaces by either electrostatic, hydrophobic, van der Waals, covalent or most likely hydrogen bonding. The polymer attach via relatively few sites to the particles leaving long loops and tails which stretch out into the surrounding liquid phase. Increase in emulsifier concentration may avoid this phenomenon and droplet size decreases when the speed increases.

The results show the influence of process parameters on droplet size distribution, $d_{3,2}$, $d_{4,3}$, and on the SPAN when silicone wax particles were stabilised by the mentioned emulsifiers.

Comparative Example 4

Preparation of Silicone Wax Colloidal Dispersions Using High Pressure Homogeniser The same raw materials were used as in example 3. Emulsions were prepared with deionised water and up to 1% emulsifier as the continuous phase and 5% of silicone wax as the disperse phase. Silicone wax was melted at about 80° C.-90° C. The continuous phase was also heated to 80° C.-90° C. to match the temperature of the disperse phase. One sample additionally contained a perfume. The dispersed phase was then added to the continuous phase and homogenised at 13,500 rpm for 5-20 minutes using a rotor-stator system (Ultra Turrax T25 basic (IKA-WERKE GmbH & Co. KG, Staufen, Germany) to form a coarse emulsion. Homogenisation of the coarse emulsion was carried out in a double sealed beaker connected to a water bath to ensure the temperature was maintained above the melting points of the waxes. After homogenisation of the coarse emulsion, it was immediately further homogenised at 1,200 bar for approximately 2 cycles using the high pressure homogeniser Microfluidizer M-110S (Microfluidics Internationalional Corporation, MA-Newton, USA). Samples were collected in sterile containers and left on the bench for cooling until samples reached room temperature (20° C.). Flow rate was about 4 to 6 mL per second.

Three emulsions were produced, of which the average particle size was determined. The compositions and results are given in the following table.

TABLE 7

Composition and average dispersed particle diameter of emulsions containing silicone wax, produced using Microfluidizer.

| Ingredient | sample 1 | sample 2 | sample 3 |
|---|---|---|---|
| water [wt %] | 94 | 94 | 91.5 |
| silicone wax SilCare 41M65 [wt %] | 5 | 5 | 5 |
| oil-based perfume [wt %] | 0 | 0 | 2.5 |
| emulsifier Tween 20 [wt %] | 0 | 1 | 0 |
| emulsifier PET-POET [wt %] | 1 | 0 | 1 |
| $d_{3,2}$ [micrometer] | 0.12 | 0.17 | 0.28 |

When comparing the dispersions produced using the CDDM-apparatus and the Microfluidizer, the CDDM-produced material had a final dispersed phase fraction about least 12-fold higher, and at a pressure 20 to 25-fold lower pressure drop.

The invention claimed is:

1. A method for production of a water-continuous emulsion,
wherein the dispersed phase of the emulsion comprises a lipophilic compound, and
wherein the mean Sauter diameter of the dispersed phase is less than 1 micrometer, and
wherein the concentration of the dispersed phase is at least 20% by weight of the emulsion, and
wherein the method comprises the steps:
(a) mixing water and an oil-in-water emulsifier to form an aqueous phase; and (b) bringing the lipophilic compound into a liquid form to form a lipophilic phase; and
(c) mixing the aqueous phase from step a) and the lipophilic phase from step b) in a distributive and dispersive mixing apparatus of the
Controlled Deformation Dynamic Mixer type or Cavity Transfer Mixer type to create a water-continuous emulsion,
and wherein the mixer is suitable for inducing extensional flow in a liquid composition,
and wherein the mixer comprises closely spaced relatively moveable confronting surfaces at least one having a series of cavities therein in which the cavities on each surface are arranged such that, in use, the cross-sectional area for flow of the liquid successively increases and decreases by a factor of at least 3 through the apparatus.

2. A method according to claim 1, wherein in step the temperature of the mixture is maximally 110° C.

3. A method according to claim 1, wherein in step b) the lipophilic compound is brought into a liquid form by increase of temperature to melt the compound.

4. A method according to claim 1, wherein the lipophilic compound comprises lecithin, fatty acid, monoglyceride, diglyceride, triglyceride, phytosterol, phytostanol, phytosteryl-fatty acid ester, phytostanyl-fatty acid ester, wax, fatty alcohol, carotenoid, oil-soluble colourant, oil-soluble vitamin, oil-soluble flavour, oil-soluble fragrance, oil-soluble drugs, mineral oils or derivatives, petrolatum or derivatives, or silicon oils or derivatives, or combinations of these compounds.

5. A method according to claim 1, wherein the lipophilic compound is selected from the group of phytosterols, carotenoids, and derivatives of these compounds.

6. A method according to claim 1, wherein in step b) the lipophilic compound is mixed with a non-aqueous phase.

7. A method according to claim 6, wherein the concentration of the lipophilic compound in the non-aqueous phase is at least 5% by weight, preferably at least 10% by weight, preferably at least 20% by weight.

8. A method according to claim 1, wherein in a subsequent step the mixture from step c) is cooled.

9. A method according to claim 1, wherein the mean Sauter diameter of the dispersed phase is less than 500 nanometer.

10. A method according to claim 1, wherein the concentration of the dispersed phase is at least 40% by weight of the emulsion, preferably at least 60% of the emulsion.

11. A method according to claim 1, wherein in step c) the Controlled Deformation Dynamic Mixer or Cavity Transfer Mixer comprises two confronting surfaces (1, 2), spaced by a distance (7),
wherein the first surface (1) contains at least three cavities (3), wherein at least one of the cavities has a depth (9) relative to the surface (1),
wherein the second surface (2) contains at least three cavities (4) wherein at least one of the cavities has a depth (10) relative to the surface (2),
wherein the cross-sectional area for flow of the liquid available during passage through the apparatus successively increases and decreases at least 3 times, and
wherein the surface (1) has a length (5) between two cavities, and
wherein the surface (2) has a length (6) between two cavities, and
wherein the surfaces (1, 2) are positioned such that the corresponding lengths (5, 6) overlap to create a slit having a length (8) or do not overlap creating a length (81),
wherein the cavities are arranged such that the cross-sectional area for flow of the liquid available during passage through the apparatus successively increases in the cavities and decreases in the slits by a factor of at least 3, and
wherein the distance (7) between the two surfaces (1,2) is between 2 micrometer and 300 micrometer, and wherein either the ratio between the length (8) and the distance (7) between the two surfaces (1, 2) ranges from 0 to 250,
or wherein the ratio between the length (81 and the distance (7) between the two surfaces (1, 2) ranges from 0 to 30.

12. A method according to claim 1, wherein the mixer is operated at a pressure less than 200 bar.

13. A method according to claim 1, wherein one of the surfaces rotates relative to the other surface at frequency between 1,000 and 25,000 rotations per minute.

* * * * *